US008836948B2

(12) United States Patent
Liu

(10) Patent No.: US 8,836,948 B2
(45) Date of Patent: Sep. 16, 2014

(54) HIGH RESOLUTION STRUCTURED ILLUMINATION MICROSCOPY

(75) Inventor: Zhaowei Liu, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 372 days.

(21) Appl. No.: 13/146,550

(22) PCT Filed: Jan. 28, 2010

(86) PCT No.: PCT/US2010/022443
§ 371 (c)(1),
(2), (4) Date: Nov. 29, 2011

(87) PCT Pub. No.: WO2010/088418
PCT Pub. Date: Aug. 5, 2010

(65) Prior Publication Data
US 2012/0069344 A1    Mar. 22, 2012

Related U.S. Application Data

(60) Provisional application No. 61/148,209, filed on Jan. 29, 2009, provisional application No. 61/148,185, filed on Jan. 29, 2009.

(51) Int. Cl.
| | |
|---|---|
| *G01B 9/02* | (2006.01) |
| *G01N 21/55* | (2014.01) |
| *G02B 27/60* | (2006.01) |
| *G02B 5/00* | (2006.01) |
| *G01N 21/64* | (2006.01) |
| *G01B 11/24* | (2006.01) |
| *G01B 9/04* | (2006.01) |
| *G02B 21/16* | (2006.01) |

(52) U.S. Cl.
CPC ........ *G02B 21/16* (2013.01); *G01N 2201/0635* (2013.01); *G02B 27/60* (2013.01); *G01N 2201/0675* (2013.01); *G02B 5/008* (2013.01); *G01N 21/648* (2013.01); *G01N 21/6458* (2013.01); *G01B 11/2441* (2013.01); *G01B 9/04* (2013.01)
USPC .......................................... 356/450; 356/445

(58) Field of Classification Search
USPC .......................... 356/445, 450; 359/370, 371
See application file for complete search history.

(56) References Cited

U.S. PATENT DOCUMENTS

| | | | |
|---|---|---|---|
| RE38,307 E | 11/2003 | Gustafsson et al. | |
| 6,873,417 B2 * | 3/2005 | Bahatt et al. | 356/445 |

(Continued)

FOREIGN PATENT DOCUMENTS

| | | |
|---|---|---|
| WO | WO-03001869 A2 | 1/2003 |
| WO | WO-03016781 A2 | 2/2003 |

(Continued)

OTHER PUBLICATIONS

PCT International Search Report dated Jun. 30, 2010, for corresponding PCT application No. PCT/US2010/022443.

(Continued)

*Primary Examiner* — Michael A Lyons
(74) *Attorney, Agent, or Firm* — Mintz, Levin, Cohn, Ferris, Glovsky & Popeo, P.C.

(57) ABSTRACT

Disclosed are systems, apparatus, methods and devices, including a method that includes generating two or more sequential surface plasmon interference patterns, at least one of the two or more sequential surface plasmon interference patterns being different from another of the two or more sequential surface plasmon interference patterns, and capturing respective images of a specimen resulting from the interference patterns. Also disclosed is a method that includes generating two or more sequential optical interference patterns, at least one of the two or more sequential optical interference patterns being different from another of the interference patterns, and removing from each of the generated interference patterns, using a beam stopper, a corresponding zero-order diffraction light component included in the respective generated patterns to obtain resultant corresponding two or more sequential optical interference patterns, directed at a specimen, with missing respective zero-order light components.

18 Claims, 11 Drawing Sheets

(56) References Cited

U.S. PATENT DOCUMENTS

| | | | |
|---|---|---|---|
| 7,084,980 B2* | 8/2006 | Jones et al. | 356/445 |
| 7,251,040 B2* | 7/2007 | Eah et al. | 356/498 |
| 8,610,897 B2* | 12/2013 | Berguiga et al. | 356/487 |
| 2003/0219809 A1 | 11/2003 | Chen et al. | |
| 2006/0119859 A1 | 6/2006 | Su et al. | |
| 2008/0069467 A1 | 3/2008 | Schafer et al. | |
| 2008/0158668 A1 | 7/2008 | Ouchi et al. | |
| 2008/0192337 A1 | 8/2008 | Osawa et al. | |
| 2008/0292135 A1 | 11/2008 | Schafer et al. | |
| 2009/0059360 A1* | 3/2009 | Evans et al. | 359/370 |

FOREIGN PATENT DOCUMENTS

| | | |
|---|---|---|
| WO | WO-03042748 A1 | 5/2003 |
| WO | WO-2007011876 A1 | 1/2007 |
| WO | WO-2007081913 A2 | 7/2007 |

OTHER PUBLICATIONS

E. Betzig, J. K. Trautman, T. D. Harris, J.S. Weiner, R.L. Kostelak, "Breaking the diffraction barrier—optical microscopy on a nanometric scale," *Science*, 251, 1468-1470, 1991.
D. Couijon, *Near-field microscopy and near-field optics* (Imperial College Press, 2003).
M. A. Paesler, P. J. Moyer, C. J. Jahncke, C. E. Johnson, R. C. Reddick, R. J. Warmack, T. L. Ferrell, "Analytical photon scanning tunneling microscopy," *Phys. Rev. B* 42, 6750-6753, 1990.
S. Hell, J. Wichmann, "Breaking the diffraction resolution limit by stimulated emission: stimulated-emission-depletion fluorescence microscopy," *Opt. Lett.* 19, 780-782, 1994.
S. Hell, "Toward fluorescence nanoscopy," *Nature Biotechnology* 21, 1347-1355, 2003.
E. Betzig, G. H. Patterson, R. Sougrat, 0. W. Lindwasser, S. Olenych, J. S. Bonifacino, M. W. Davidson, J. Lippincott-Schwartz, H. F. Hess, "Imaging intracellular fluorescent proteins at nanometer resolution," *Science*, 313, 1642-1645, 2006.
M. J. Rust, M. Bates, X. W. Zhuang, "Sub-diffraction-limit imaging by stochastic optical reconstruction microscopy (STORM)," *Nature Method* 3, 793-795, 2006.
J. Gelles, B. J. Schnapp, M. P. Sheetz, "Tracking kinesin-driven movements with nanometer-scale precision," *Nature* 331, 450-453, 1988.
A. Yildiz, J. N. Forkey, S. A. Mckinney, T. Ha, Y. E. Goldman; P. R. Selvin, "Myosin V walks hand-overhand: Single fluorophore imaging with 1.5-nm localization," *Science* 300, 2061-2065, 2003.
B. Huang, W. Wang, M. Bates, X. Zhuang, "Three-Dimensional Super-Resolution Imaging by Stochastic Optical Reconstruction Microscopy," *Science*; 319, 810-813, 2008.
M. Bates, B. Huang, G. T. Dempsey, X. Zhuang, "Multicolor Super-Resolution Imaging with Photo-Switchable Fluorescent Probes," *Science* 317, 1749-1753, 2007.
A. Sharonov, R. M. Hochstrasser, "Wide-field subdiffraction imaging by accumulated binding of diffusing probes," *PNAS*, 103, 18911-18916, 2006.
D. Wu, Z. Liu, C. Sun, X. Zhang, "Super-resolution imaging by random adsorbed molecule probes," *Nano. Lett.* 8, 1159-1162, 2008.
X. Zhang, Z. Liu, "Superlenses to overcome the diffraction limit," *Nature Materials*. 7,435--441, 2008.
S. Durant, Z. Liu, J. M. Steele, X. Zhang, Theory of the transmission properties of an optical far-field superlens for imaging beyond the diffraction limit, *J. Opt. Soc. Am. B*. 23, 2383-2392, 2006.
Z. Liu, S. Durant, H. Lee, Y. Xiong, Y. Pikus, C. Sun, X. Zhang, "Near-field Moire effect mediated by surface plasmon polariton excitation," *Opt. Lett.* 32, 629-631, 2007.
Z. Liu, S. Durant, H. Lee, Y. Pikus, N. Fang, Y. Xiong, C. Sun, X. Zhang, "Far field optical superlens," *Nano. Lett.* 7, 403-408, 2007.
H. Lee, Z. Liu, S. Durant, Y. Xiong, C. Sun, X. Zhang, "Design, fabrication and characterization of far-field superlens," *Solid State Commun.* 146, 202-207, 2008.

Z. Liu, H. Lee, Y. Xiong, C. Sun, X. Zhang, "Optical hyperlens magnifying sub-diffraction-limited objects," *Science* 315, 1686, 2007.
H. Lee, Z. Liu, Y. Xiong, C. Sun, X. Zhang, "Development of optical hyperlens for imaging below the diffraction limit," *Opt. Express* 15, 15886-15891, 2007.
M. G. L. Gustafsson, "Surpassing the lateral resolution limit by a factor of two using structured illumination microscopy," *J. Microsc.* 198, 82-87, 2000.
R. Heintzmann, C. Cremer, "Laterally modulated excitation microscopy: improvement of resolution by using a diffraction grating," *Proc. SPIE* 3568, 185-195, 1998.
J. T. Frohn, H. F. Knapp, A. Stemmer, "True optical resolution beyond the Rayleigh limit achieved by standing wave illumination,", *PNAS* 97, 7232-7236, 2000.
R. Heintzmann, T. M. Jovin, C. Cremer, "Saturated patterned excitation microscopy—a concept for optical resolution improvement," *J. Opt. Soc. Am. A* 19, 1599-1609, 2002.
M. G. L. Gustafsson, "Nonlinear structured-illumination microscopy: wide-field fluorescence imaging with theoretically unlimited," *PNAS*, 102, 13081-13086, 2005.
M. G. L. Gustafsson, L. Shao, P. M. Carlton, C. J. R. Wang, I. N. Golubovskaya, W. Z. Cande, D. A. Agardt, J. W. Sedat, "Three-dimensional resolution doubling in wide-field fluorescence microscopy by structured illumination," *Biophys. J.* 94, 4957-4970, 2008.
L. Schermelleh, P. M. Carlton, S. Haase, L. Shao, L. Winoto, P. Kner, B. Burke, M. C. Cardoso, D. A. Agard, M. G. L. Gustafsson, H. Leonhardt, J. W. Sedat, "Subdiffraction multicolor imaging of the nuclear periphery with 3D structured illumination microscopy," *Science*, 320, 1332-1336, 2008.
H. Raether, *Surface plasmon on smooth and rough surface and on gratings*, Springer-Verlag, 1988.
F. Keilmann, K. W. Kussmaul, Z. Szentirmay, "Imaging of optical watertrains," *Appl. Phys. B: Photophys. Laser Chem.* 47, 169-172, 1988.
Salerno, N. Fe'lidj, J. R. Krenn, A. Leitner, F. R. Aussenegg J. C. Weeber, "Near-field optical response of a two-dimensional grating of gold nanoparticles," *Phys. Rev. B* 63, 165422, 2001.
X. G. Luo, T. Ishihara, "Surface plasmon resonant interference nanolithography technique," *Appl. Phys. Lett.* 84, 4780-4782, 2004.
X. G. Luo, T. Ishihara, "Subwavelength photolithography based on surface-plasmon polariton resonance," *Opt. Express* 12, 3055-3065, 2004.
Z. Liu, Q. H. Wei, X. Zhang, "Surface plasmon interference nanolithography," *Nano. Lett.* 5, 957-961, 2005.
Z. Liu, J. M. Steele, W. Srituravanich, Y. Pikus, C. Sun, X. Zhang, "Focusing surface plasmons with a plasmonic lens," *Nano. Lett.* 5, 1726-1729, 2005.
Z. Liu, J. M. Steele, H. Lee, X. Zhang, "Tuning the focus of a plasmonic lens by the incident angle," *Appl. Phys. Lett.* 88, 171108, 2006.
O. Kafri, I. Glatt, *The physics of Moire Metrology*. Wiley, 1989.
C. A. Walker, *Handbook of Moire measurement*. IoP Bristol and Philadelphia, 2004.
D. C. Flanders, H. I. Smith, S. Austin, "A new interferometric alignment technique," *Appl. Phys. Lett.* 31, 426-428, 1977.
Z. Liu, S. Durant, H. Lee, X. Xiong, Y. Pikus, C. Sun, X. Zhang, "Near-field Moire effect mediated by surface plasmon polariton excitation," *Opt. Lett.* 32, 629-631, 2007.
S. W. Hell, "Far-field optical nanoscope," *Science*, 316, 1153-1158, 2007.
C. Nylander, B. Liedberg, T. Lind, "Gas detection by means of surface plasmon resonance," *Sensors and Actuators* 3, 79-88, 1982.
J. Homola, S. S. Yee, G. Gauglitz, "Surface plasmon resonance sensors: review," *Sensors and Actuators B* 54, 3-15, 1999.
W. Hickel, D. Kamp, W. Knoll, "Surface plasmon microscopy," *Nature* 339, 186-186, 1989.
J. M. Brockman, B. P. Nelson, R. M. Corn, "Surface plasmon resonance imaging measurements of ultrathin organic films," *Annu. Rev. Phys. Chem.* 51, 41-63, 2000.

(56) References Cited

OTHER PUBLICATIONS

K. Kneipp, Y. Wang, H. Kneipp, L. T. Perelman, I. Itzkan, R. R. Dasari, M. S. Feld, "Single molecule detection using surface-enhanced Raman scattering (SERS)" *Phys. Rev. Lett.* 78, 1667-1670, 1997.

S. M. Nie, S. R. Emery, "Probing single molecules and single nanoparticles by surface-enhanced Raman scattering," *Science* 275, 1102-1104, 1997.

A. Wokaun, J. G. Bergman, J. P. Heritage, A. M. Glass, P. F. Liao, D. H. Olson, "Surface second-harmonic generation from metal island films and microlithographic structures," *Phys. Rev. B* 24, 849-856, 1981.

C. K. Chen, A. R. B. de Castro, Y. R. Shen, "Surface-enhanced second- harmonic generation," *Phys. Rev. Lett.* 46, 145-148, 1981.

E. M. Kim, S. S. Elovikov, T. V. Murzina, A. A. Nikulin, O. A. Aktsipetrov, M. A. Bader, G. Marowsky, "Surface-enhanced optical third-harmonic generation in Ag island films," *Phys. Rev. Lett.* 95, 227402, 2005.

N. Fang, H. Lee, C. Sun, X. Zhang, "Sub-Diffraction-Limited Optical Imaging with a Silver Superlens," *Science* 308, 534-537, 2005.

D. O. S. Melville, R. J. Blaikie, "Super-resolution imaging through a planar silver layer," *Opt. Express* 13, 2127-2134, 2005.

R. Zia, M. D. Selker, M. L. Brongersma, "Leaky and bound modes of surface plasmon waveguides," *Phys. Rev. B.* 71, 165431, 2005.

W. L. Barnes, A. Dereux, T. W. Ebbesen, "Surface plasmon subwavelength optics," *Nature*, 424, 824-830, 2003.

D. P. F. Pile, D. K. Gramotnev, "Channel plasmon-polariton in a triangular groove on a metal surface," *Opt. Lett.* 29, 1069-1071, 2004.

S. I. Bozhevolnyi, V. S. Volkov, E. Devaux, J. Y. Laluet, T. W. Ebbesen, "Channel plasmon subwavelength waveguide components including interferometers and ring resonators," *Nature*, 440, 508-511, 2006.

W. Srituravanich, N. Fang, C. Sun, Q. Luo, X. Zhang, "Plasmonic nanolithography," *Nano Lett.* 4, 1085-1088, 2004.

D. B. Shao, S. C. Chen, "Surface-plasmon-assisted nanoscale photolithography by polarized light," *Appl. Phys. Lett.* 86, 253107, 2004.

L. Wang, S. M. Uppuluri, E. X. Jin, X. F. Xu, "Nanolithography using high transmission nanoscale bowtie apertures,," *Nano Letters* 6, 361-364, 2006.

C. Sonnichsen, B. M. Reinhard, J. Liphardt, A. P. Alivisatos, "A molecular ruler based on plasmon coupling of single gold and silver nanoparticles," *Nature Biotechnology* 23, 741-745, 2005.

J. Yao, Z. Liu, Y. Liu, Y. Wang, C. Sun, G. Bartal, A. Stacy, X. Zhang, "Optical negative refraction in bulk metamaterials," *Science*, 321, 930, 2008.

D. P. O'Neal, L. R. Hirsch, N. J. Halas, J.D. Payne, J.L. West, "Photo-thermal tumor ablation in mice using near infrared-absorbing. nanoparticles," *Cancer Lett.* 109, 181-176, 2004.

Y. Xiong, Z. Liu, C. Sun, X. Zhang, "Two dimensional imaging by far-field superlens at visible wavelength", *Nano. Lett.* 7, 3360-3365, 2007.

Y. Xiong, Z. Liu, X. Zhang, "Projecting deep-subwavelength patterns from diffraction-limited masks using metal-dielectric multilayers," *Appl. Phys. Lett.* 93, 111-116, 2008.

S. Takahashi, S. Okada, H. Nishioka, S. Usuki, K. Takamasu, "Theoretical and numerical analysis of lateral resolution improvement characteristics for fluorescence microscopy using standing evanescent light with image retrieval", *Meas. Sci. Technol.* 19, 084006, 2008.

R. Fiolka, M. Beck, A. Stemmer, "Structured illumination in total internal reflection fluorescence microscopy using a spatial light modulator", *Opt. Lett.* 33, 1629-1931, 2008.

J. W. Goodman, *Introduction to Fourier Optics*. Robert & Company Publishers, Third edition, copyright 1996.

\* cited by examiner

HIGH RESOLUTION STRUCTURED ILLUMINATION MICROSCOPY

CROSS-REFERENCE TO RELATED APPLICATIONS

This application claims priority to provisional U.S. application Ser. No. 61/148,209, entitled "High Speed Laser Interference Structure Illumination Microscopy" and filed Jan. 29, 2009, and to U.S. Provisional application Ser. No. 61/148,185, entitled "High Speed Plasmonic Structured Illumination Microscopy," and filed Jan. 29, 2009, the contents of which are hereby incorporated by reference in their entireties.

BACKGROUND

The subject matter described herein relates to optical microscopy, and more particularly to systems, apparatus, devices and methods for high-resolution optical microscopy based on structure illumination microscopy procedures.

Modern optical microscopy has been key to advancing understanding of structures and functions in living cells. However, one disadvantage has been its diffraction-limited spatial resolution (resolving only features no smaller than half the wavelength used).

Several techniques have been developed to improve the resolution. Near-field scanning optical microscopy (NSOM) forms high resolution images by scanning a sharp tip in the close vicinity of an object. With the access to the optical near field, the resolution is limited by the sharpness of the tip rather than the conventional diffraction. Stimulated emission depletion (STED) microscope is another technique to overcome the diffraction limit by utilizing stimulated emission to sharpen the fluorescence focal spot. Both techniques require the time-consuming point-by-point scanning process, which limits their use in real-time imaging. Another family of the techniques, such as photoactivatable localization microscopy (PALM), stochastic optical reconstruction microscopy (STORM), randomly adsorbed molecule microscopy (RAM), which based on the single molecular localization methods, has been emerged mainly in the last few years as a powerful tool to image at deep sub-wavelength scale. The significant spatial resolution improvement, however, has to come with severe imaging speed deterioration. The time for one frame of image is typically about a few minutes or more.

Another emerging field is the superlens and hyperlens imaging approach. Because this technique is based on a projection imaging system, an advantage, in some implementations, of this approach is its ability to go beyond the conventional diffraction limit without affecting too much of the imaging speed.

Structured illumination microscopy (SIM) is another promising technique that has shown great success in fluorescent microscopy. SIM superposes a light pattern on an object with sub-wavelength features to produce fringe patterns which can be optically measured and processed to form a high-resolution image. Significant spatial resolution improvement can be gained using these techniques but with low imaging speed being a trade-off. Standard or linear SIM generally offers a factor of two (2) resolution improvement because the illumination pattern used is diffraction-limited. Non-linear SIM applied to fluorescence microscopy achieves >2 resolution enhancement by introducing higher harmonics to the illumination pattern through the nonlinear, saturated fluorescence response. This technique, however, entails additional limitations (e.g., sample heating/damage, need to acquire more images) and is generally not applicable to scattering microscopy.

SUMMARY

The subject matter described herein relates to optical microscopy, and in particular to structured illumination microscopy. An objective of the subject matter described herein is to develop a high-resolution and high-speed optical imaging tool and methodology to enable nano-scale observations of fundamental processes that occur in native dynamic systems.

The systems, apparatus, devices and methods described herein overcome the performance barriers discussed above by using rapidly programmable light interference patterns with enhanced periodicities. It can be implemented for both scattering and fluorescence microscopy, including non-linear SIM, with unique advantages of super resolution and high speed for 3D fluorescence imaging.

By combining two emerging fields, namely, the field of tunable surface plasmon interference and the field of structured illumination microscopy, the microscopy described herein may, in some implementations, possess unprecedented performance and may represent a new milestone in light imaging microscopy.

The subject matter disclosed herein provides methods, systems, apparatus, devices and articles of manufacture for optical microscopy. In one aspect, optical microscopy may be based on using structured illumination, with the structured illumination of a sample/specimen being achieved through interference patterns generated by surface plasmons.

The description herein relates to an optical imaging technique to achieve high spatial resolution and high speed by integrating the structured illumination concept with the controllable surface plasmon interference (SPI) patterns. SPI may be applied in photolithography and other sensing structures to obtain deep sub-wavelength resolution. Because the surface plasmon waves have smaller wavelength than the excitation light with the same frequency, the SPI patterns can obtain high resolution to enable further improvements of imaging resolution in SIM. The combination of SPI with SIM may thus lead to remarkable possibilities, since the gain of the resolution does not have to be associated with, for example, nonlinear responses in fluorescent dyes, thus leading to significant flexibility for the applications, and more importantly avoiding the need of a large number of data acquisitions.

High resolution SPI has been experimentally demonstrated for various wavelengths. The numerical simulations of plasmonics structured illumination microscopy (PSIM) has also been performed, with the results showing significant resolution improvement. In some implementations, PSIM may enable direct imaging of samples with super resolution (3-5 fold improvement compared with conventional optical microscopy). As described herein, a high speed surface plasmon interference pattern control may be implemented by using a high speed digital mirror device (DMD), leading to a final reconstructed imaging at ultra-fast speed. The subject matter disclosed herein describes a unique tool for sub-wavelength imaging and characterization on a well controlled optical illumination microscope instrument. In some implementations, ultra-fast dynamic imaging with sub-diffraction limited resolution for both scattering microscopy and fluorescent microscopy may be achieved.

Also disclosed herein are methods, systems, devices and apparatus to perform fast, nanoscale optical microscopy using structured illumination provided by tunable plasmon interference patterns. Surface plasmons—electromagnetic waves formed by collective oscillations of electrons at a metal/dielectric interface—propagate such that their wavelength is shorter than that of light of the same frequency. Hence, plasmons enable illumination patterns with spatial resolution superior to those attainable by direct use of light and standard optics. In some implementations, multiple measurements with different phase-shifts between a sample and illumination patterns are obtained by varying the angle of incidence of the excitation laser beam(s) upon the metal surface to tune the phase of the plasmon waves. The incident angle control is implemented using a fast, programmable space light modulator, e.g., a digital micro-mirror device, electro-optical, acoustic-optical or liquid crystal modulator, thus making high-speed data acquisition and dynamic imaging studies possible. PSIM can achieve at least 3 to 5 fold spatial resolution improvement compared with conventional optical microscopy and imaging speeds of ≥50 frames/second.

The subject matter described herein may establish an optical instrument for deep sub-wavelength spatial resolution imaging at ultra-fast speed. By combining the two emerging fields, e.g., structured illumination microscopy and controllable surface plasmon interference, the entirely new capabilities provided by the PSIM will contribute to the study in the fields of physical science, material science, biomedical imaging and any other fields where high resolution high speed optical imaging is needed. Imaging tools based on PSIM may obtain high resolution in both space (sub 100 nanometers scale) and time (ms or sub-ms scale) simultaneously.

In some implementations, one or more of the following features may be provided. For example, a method of optical microscopy may be provided. The method may use structured illumination, wherein the illumination of a specimen is provided by interference patterns generated by surface plasmons, the method referred to as plasmonic structured illumination microscopy (PSIM). The plasmon interference patterns may be obtained at a metal/dielectric interface by using slits, gratings or other surface features incorporated into a metal layer to convert free space light (the excitation light) into surface-confined plasmons, wherein the type of metal and excitation light wavelength are chosen and the surface features are dimensioned, shaped and arranged so the plasmons from each surface feature may overlap to create an interference pattern with periodicity shorter than the wavelength of the excitation light. The characteristics of the plasmon interference pattern may be further controlled by the polarization and angle of incidence of the excitation light relative to the metal/dielectric interface. The images recorded may include different Moire fringes formed when illuminating the specimen using plasmon interference patterns with different phases (or using different plasmon interference patterns), which images are then processed to reconstruct an image of the specimen. A system may implement one of more of the aforementioned features using a conventional optical microscope as a platform and incorporating: an excitation light source; a component that enables the conversion of excitation light into surface plasmons; optical components (e.g., lenses, mirrors, space light modulator) that steer, split or otherwise control or modify the beams derived from the excitation light source as needed for their use with the microscope and the light-to-plasmon converting component; and an image recording device. Moreover, the system may use a dual, opposing objectives microscope configuration, where the excitation light beam is steered and controlled through a first objective while the specimen is observed and its image collected through a second objective. The system may also use a "plasmonic structure insert" to convert free space light into surface plasmons and create plasmonic interference patterns, the insert being constituted by at least one metal/dielectric stack, e.g., optically thick metal film on glass, or metal/dielectric multi-layer on glass, where the metal film incorporates an arrangement of surface features (e.g., slits, gratings, etc.) The plasmonic structure insert may be positioned between the two opposing objectives with the metal surface facing the second objective so the excitation light issuing from the first objective is received by the surface features in the metal layer(s) but is otherwise blocked by the metal layer(s) and the plasmonic interference pattern is formed in the specimen plane between the metal surface and the second objective. The system may include a fast, programmable space light modulator, a digital micro-mirror device, electro-optical, acoustic-optical or liquid crystal modulator, used to vary the angle of incidence of the excitation laser beam(s) upon the metal surface to tune the phase of the plasmon waves. The system may include metal used in the insert is Au, Ag or Al and the excitation light may have a wavelength of 365 nm.

Also disclosed herein are methods and apparatus applying said method to perform fast, nanoscale optical microscopy using structured illumination provided by programmable, periodicity-enhanced light interference patterns. In some implementations, the illumination patterns are formed by a periodic plurality of beams generated by a computer-controlled space light modulator, e.g., a digital micro-mirror device, electro-optical, acoustic-optical or liquid crystal modulator, upon irradiation of the modulator by collimated coherent light, typically from a laser. Under computer control, the periodicity and orientation of the beams can be changed rapidly to facilitate the multiple measurements with different phase-shifts between specimen and illumination patterns that are needed for high-resolution image reconstruction, thus making high-speed data acquisition possible (≥50 frames/second). Further, the periodicity of the interference pattern illuminating the specimen can be enhanced (e.g., doubled) by suppressing the central or other lower-order (e.g., zero-order) light of the plurality of beams as they are steered into the microscope. In this manner, spatial resolution gain factors >3 relative to standard optical microscopy can be achieved in all three dimensions without compromising the imaging speed.

The subject matter described herein may be implemented to include one or more of the following features. A method of microscopy using structured illumination where the illumination is provided by programmable, periodicity-enhanced light interference patterns. The interference patterns are formed by a periodic, plurality of beams generated from a space light modulator, e.g., a digital micro-mirror device, electro-optical, acoustic-optical or liquid crystal modulator, upon irradiation by collimated coherent light. The periodicity and orientation of the beams can be changed rapidly under computer control of the space-light modulator. The periodicity of the interference pattern illuminating the specimen is enhanced by suppressing the central and/or lower-order light components of the plurality of beams forming the interference pattern. The images recorded may include different Moire fringes formed when illuminating the specimen using interference patterns with different phases or different patterns, which images are then processed to reconstruct an image of the specimen. A system applying the aforementioned methods may use a conventional optical microscope as a platform and incorporating: an excitation light source; optical components (e.g., lenses, mirrors, space light modulator, beam stops or masks) that steer, split or otherwise control and/or modify the beams derived from the excitation light source as needed for their use with the microscope and suppression of lower-order light; and, an image recording device.

In one aspect, a method is disclosed. The method includes generating two or more sequential surface plasmon interference patterns, at least one of the two or more sequential surface plasmon interference patterns being different from another of the two or more sequential surface plasmon interference patterns, and capturing respective images of a specimen resulting from each of the two or more surface plasmon interference patterns.

Embodiments of the method may include any of the following features.

The method may further include generating a reconstructed image of the specimen based on the captured respective images of the specimen resulting form the two or more surface plasmon interference patterns.

Generating the two or more sequential surface plasmon interference patterns may include applying optical radiation at a medium, the medium being configured to generate surface plasmons upon application of optical radiation thereon. Applying optical radiation at the medium may include applying optical radiation at the medium at respective two or more angles corresponding to the two or more surface plasmon interference patterns, at least one of the two or more angles being different from another of the two or more angles. Applying optical radiation at the medium may include applying optical radiation comprising two or more optical interference patterns, at least one of the two or more optical interference patterns being different from another of the two or more optical interference patterns.

Applying optical radiation at the medium may include directing the optical radiation at the medium using a modulator to modulate optical energy received by the modulator. The modulator may include one or more of, for example, a digital mirror device, an electro-optical modulator, an acoustic-optical modulator, a liquid crystal modulator, and/or an optomechanical modulator.

The medium configured to generate surface plasmons upon application of optical radiation thereon may include a metal/dielectric interface with at least one surface feature defined thereon. The at least one surface features may include one or more of, for example, at least one slit, and/or at least one grating.

In another aspect, a system is disclosed. The system includes an energy source to generate energy, a controller to cause the generated energy to be applied at a medium configured to generate surface plasmons so as to generate two or more sequential surface plasmon interference patterns, at least one of the two or more sequential surface plasmon interference patterns being different from another of the two or more sequential surface plasmon interference patterns, and a capturing device to capture respective images of a specimen resulting from each of the two or more surface plasmon interference patterns.

Embodiments of the system may include one or more of the above-described features of the method, as well as any of the following features.

The two or more sequential surface plasmon interference patterns may include at least one of the two or more plasmon interference patterns having a phase different from another phase of another of the two or more surface plasmon interference patterns.

The system may further include a processor to generate a reconstructed image of the specimen based on the captured respective images of the specimen resulting from the two or more surface plasmon interference patterns.

The controller configured to cause the generated energy to be applied at the medium so as to generate two or more sequential surface plasmon interference patterns may be configured to apply optical energy at the medium.

The controller configured to apply optical energy may be configured to apply optical energy generated by the optical energy source at the medium at respective two or more angles corresponding to the two or more surface plasmon interference patterns, at least one of the two or more angles being different from another of the two or more angles, each of the interference patterns of the two or more surface plasmon interference patterns being generated based, at least in part, on the respective two or more angles applied to the medium.

The controller configured to apply optical energy may be configured to apply two or more optical interference patterns at the medium, at least one of the two or more optical interference patterns having a pattern different than another pattern of another of the two or more optical interference patterns.

The controller may include a modulator including one or more of, for example, a digital mirror device, an electro-optical modulator, an acoustic-optical modulator, a liquid crystal modulator, and/or an optomechanical modulator.

The system may further include the medium configured to generate surface plasmons.

The medium may include a metal/dielectric interface with at least one surface feature defined thereon.

In a further aspect, an integrated device is disclosed. The device includes a light source, and a medium configured to generate surface plasmon interference patterns. Light from the light source is directed at the medium to cause two or more sequential surface plasmon interference patterns to be generated, at least one of the two or more sequential surface interference patterns being different from another of the two or more surface plasmon interference patterns. The generated two or more sequential surface plasmon interference patterns result in a sequence of images of a specimen that are used to reconstruct a high resolution image of the specimen.

Embodiments of the device may include one or more of the above-described features of the method and the system, as well as the following feature.

The light source may include a LED device, and the medium may include a metal/dielectric interface with at least one surface feature defined thereon.

The device may further include a controller to modulate the light from the light source and to direct the modulated light at the medium to cause the two or more sequential surface plasmon interference patterns.

In yet a another aspect, a method is disclosed. The method includes generating two or more sequential optical interference patterns, at least one of the two or more sequential optical interference patterns being different from another of the two or more sequential optical interference patterns, and removing from each of the generated two or more sequential optical interference patterns, using a beam stopper, a corresponding zero-order diffraction light component included in the respective generated two or more sequential optical interference patterns to obtain resultant corresponding two or more sequential optical interference patterns with missing respective zero-order light components, the resultant two or more sequential optical interference patterns being directed at a specimen.

Embodiments of the method may include one or more of the above-described features of the first method, the system, and the device, as well as any of the following features.

The method may further include removing at least one other low-order light component included in each of the respective generated two or more sequential optical interference patterns.

The method may further include capturing respective optical images of the specimen resulting from each of the directed resultant sequential optical interference patterns with the missing respective zero-order components.

The method may further include generating a reconstructed image of the specimen based on the captured respective optical images of the specimen.

Generating the two or more sequential optical interference patterns may include modulating optical energy from an energy source to generate the two or more sequential optical interference patterns using one or more of for example, a digital mirror device to modulate the optical energy from the optical energy source, a liquid crystal to modulate the optical energy passing through the crystal, an acoustic-optical modulator and/or an electro-optical modulator.

The optical energy source may include one or more of, for example, a laser device, and/or a lamp to generate incoherent light.

In a further aspect, a system is disclosed. The system includes an optical energy source to generate optical energy, a controllable modulator to controllably modulate the generated optical energy to generate two or more sequential optical interference patterns, at least one of the two or more sequential optical interference patterns being different from another of the two or more sequential optical interference patterns, and a beam stopper to remove from each of the generated two or more sequential optical interference patterns a corresponding zero-order diffraction light component included in the respective generated two or more sequential optical interference patterns to obtain resultant corresponding two or more sequential optical interference patterns with missing respective zero-order light components directed at a specimen.

Embodiments of the system may include one or more of the above-described features of the methods, the first system, and the device, as well as any of the following features.

the beam stopper may further be configured to remove at least one other low-order light component included in each of the respective generated two or more sequential optical interference patterns.

The system may further include a capturing device to capture respective optical images of the specimen resulting from each of the directed resultant sequential optical interference patterns with the missing respective zero-order light components.

The system may further include a processor to generate a reconstructed image of the specimen based on the captured respective optical images of the specimen.

The controllable modulator may include one or more of, for example, a digital mirror device to modulate the optical energy, a liquid crystal to modulate the optical energy passing through the crystal, an acoustic-optical modulator and/or an electro-optical modulator.

The details of one or more variations of the subject matter described herein are set forth in the accompanying drawings and the description below. Features and advantages of the subject matter described herein will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Disclosed herein are methods, systems, apparatus and devices that include a method including generating two or more sequential surface plasmon interference patterns, in which at least one of the two or more sequential surface plasmon (SP) interference patterns are different from another of the two or more sequential surface plasmon interference patterns. For example, the at least one SP interference pattern may have a phase, polarization and/or pattern that is different from the phase, polarization and/or pattern of another of the SP interference patterns. The method also includes capturing respective images (e.g., optical images) of a specimen resulting from each of the surface plasmon interference patterns. In some implementations, the surface plasmons interference patterns are generated by applying optical radiation onto a medium at respective two or more angles (controlled, for example, using an optical modulator such as, for example, a digital mirror device, an electro-optical modulator, an acoustic-optical modulator, a liquid crystal modulator, an optomechanical modulator, etc.) which in turn cause corresponding two or more surface plasmon interference patterns to be generated. The medium, for example, a metal plate with surface features (e.g., one or more slits) is configured to generate surface plasmons upon application of optical radiation on it.

Also disclosed herein are systems, apparatus, devices and methods that include a method including generating two or more sequential optical interference patterns, with at least one of the two or more sequential optical interference patterns being different from another of the two or more sequential optical interference patterns, and removing from each of the generated two or more sequential optical interference patterns, using a beam stopper, a corresponding zero-order diffraction light component (and/or other low-order light components) included in the respective generated two or more sequential optical interference patterns to obtain resultant corresponding two or more sequential optical interference patterns with missing respective zero-order light components, the resultant two or more sequential optical interference patterns being directed at a specimen.

Structured Illumination Microscopy (SIM) and Surface Plasmon Interference

Figure 1:
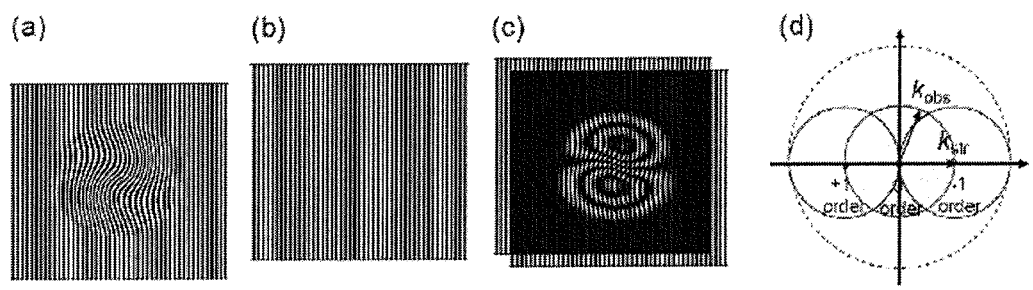
FIG. 1 is a diagram with graphs depicting the principle of structure illumination microscopy (SIM).

When a periodic illumination light pattern is overlapped with a specimen, a moiré fringe pattern is constructed (see the graphs in FIGS. 1a, 1b, and 1c). This pattern can be understood by a so-called moiré effect due to "frequency mixing" between the superimposed sample/specimen and the illumination pattern. As seen in FIG. 1(c), for example, such moiré fringes can be much coarser than either of the original patterns and in particular may be easily observable in the microscope even if one (or both) of the original patterns is too fine to resolve. Therefore, if the illumination pattern is known, one can access normally unresolvable high resolution information by the resolvable "moiré fringes." The super resolution image can be subsequently reconstructed (e.g., using a computer-based device) by measuring moiré fringes under carefully controlled illumination patterns. This is the physical foundation for the resolution extension of SIM.

To understand how SIM work, it is useful to think of the sample structure in reciprocal space, that is, its Fourier transform. In that representation, low resolution information resides close to the origin, while higher resolution information resides further away. Due to the diffraction limit, a conventional microscope can generally only detect information that resides within a circular region of radius $k_{obs}$ round the origin of the Fourier space (see FIG. 1d), which is determined by the numerical aperture (NA) of the optical system. SIM does not change the observable region, but rather moves information into the region from the outside, thus making that information observable. Assuming the periodic illumination pattern contains a spatial frequency $k_{str}$, the frequency k of the object being observed gives rise to moiré fringes at frequency $k-k_{str}$. Those fringes can be observed by conventional microscope if $k-k_{str}$ lies in the observable range ($|k-k_{str}|<k_{obs}$). Therefore, the highest observable spatial frequency (the resolution) in Fourier space is extended from $k_{obs}$ to $k_{obs}+k_{str}$, (see FIG. 1d).

As a specific example, consider an illumination pattern that includes a sinusoidal stripe profile. The Fourier transformation of such a profile includes three non-zero points representing 0, +1, and −1 diffraction orders of the illumination pattern. The image that is directly seen through a structured illumination microscope, in addition to the normal image information within the center observable circle, also comprises moiré fringes which come from the other two offset circular regions (marked as +1 order and −1 order in FIG. 1d). The overall observable information through SIM is the sum of three components from different diffraction orders.

In order to obtain a high-resolution image, the three overlapped frequency components have to be separated and relocated to the original position. This may be done by taking multiple measurements with relative phase-shifts between the sample/specimen being observed and the illumination pattern(s), followed by a data processing procedure. As the requirement of the procedure, the three unknown components can be separated by recording three or more images of the sample with different given illumination phases. By repeating this one or more times with the pattern orientated in different directions, all the information within the dotted circle may be collected to thus provide a physically observable region that is beyond that which can be observed and processed without the use of structured illumination. From another point of view, SIM can also be treated as a scanning type of imaging tool but with many probing spots that only need to scan several steps within a period. This is the underlying reason why SIM possesses higher imaging speed compared with NSOM.

Both $k_{str}$ and $k_{obs}$ are limited by the numerical aperture (NA) of the optical system. The common SIM can therefore improve the spatial resolution by a factor of two, i.e., $(k_{obs}+k_{str})/k_{obs}=2$. With nonlinear based SIM utilizing a non-sinusoidal illumination profile that comprises more than three non-zero points (0, +1, and −1 orders) in its Fourier transformation, the nonlinear SIM has the ability to access spatial frequencies up to $k_{obs}+nk_{str}$, (n is the non-zero order in the Fourier transformation of the illumination pattern). Thus, the second order nonlinear SIM can improve resolution by a factor of 3, for example. With the improvement in spatial resolution, nonlinear-SIM, however, has to deal with many of other problems. For instance, the very high light density for realizing the nonlinear response of fluorescent dyes may easily introduce damage to the sample. Also, the sampling image number scales up with $n^2$, which eventually becomes a challenge to improving imaging speed.

Nevertheless, SIM has shown a significant ability to enhance the spatial resolution and is considered to have strong potential to realize optical imaging tools at nanoscales.

Surface plasmons (SP), also known as surface plasmon polaritons (SPP), are surface electromagnetic waves formed by collective oscillation of electrons at a metal/dielectric interface. The fundamental SP properties have been extensively studied in 1970's and widely applied thereafter in a number of important applications such as surface plasmon resonance (SPR) sensing and imaging (SPRI), surface enhanced Raman scattering (SERS), surface enhanced second harmonic generation, etc. Significant advancement in nanoscale fabrication techniques, subwavelength electromagnetic wave guiding, plasmonic lithography, plasmonic ruler, optical negative refraction, as well as cancer treatment by metallic nano-particles have extended and transformed the horizon of the field of plasmonics.

Figure 2:
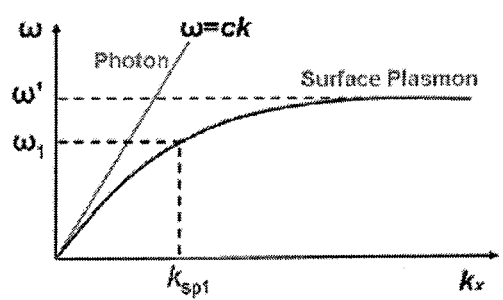
FIG. 2 is a graph of the dispersion curve of surface plasmons on a metal/dielectric interface.

The dispersion relation for SP at an interface between semi-infinite metal and dielectric materials is expressed as:

$$k_{sp} = \sqrt{\frac{\varepsilon_1 \varepsilon_m}{\varepsilon_1 + \varepsilon_m}} \frac{2\pi}{\lambda_0} \qquad (1)$$

where $k_{sp}$ is the SP wave vector, $\lambda_0$ is the light wavelength in vacuum, $\in_1$ and $\in_m$ are the permittivity of the dielectric and metal, respectively. FIG. 2 shows a typical dispersion curve of the surface plasmons on a metal/dielectric interface. As shown, the curve of SPs resides on the right-hand side of the light cone, which means that SPs corresponds to a larger wavevector (or smaller wavelength) than that of light at the same frequency. Particularly, when the frequency approaches to the resonance frequency ω', the wavelength of the SPs can be extremely small.

A light beam in three dimensional (3D) free space can be converted into a two dimensional (2D) SP wave as long as the momentum mismatch between them is compensated by a coupling element. The sacrifice of dimensionality, however, results in the so-called "optical frequency but X-ray wavelength" property, i.e. the wavelength of SPs can be much smaller than that of the excitation energy (e.g., light). As a straightforward consequence, converting free space light into SPs on a planar surface should lead to devices or applications that possess higher spatial resolution.

Figure 3:
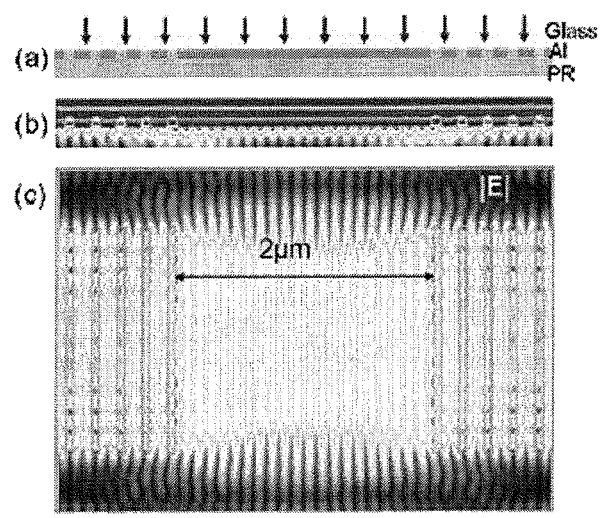
FIG. 3 includes diagrams of a schematic of a structure to form surface plasmons (SP) interference patterns and corresponding patterns.

A suitable SP coupler is a grating which can provide additional discrete wave vector in a very efficient way. If two gratings are properly arranged, the SPs generated from the two gratings may overlap to thus form a uniform interference pattern as shown in FIG. 3. FIG. 3(a) shows the schematic configuration of a structure that can be used to form SP interference pattern. The schematic in FIG. 3(a) includes an aluminum film (indicated by the symbol "Al") with a thickness of 100 nm, and a photoresist (PR) semi-infinite layer with a reflective index equal to 1.5 positioned underneath the aluminum film. FIG. 3(b) shows the simulated total light field intensity distribution in a cross-sectional view, and FIG. 3(c) is top view of the light intensity distribution. The period of the SP interference pattern, in this specific example, is about 110 nm which is much smaller than the 365 nm wavelength of the light used to excite the SP interference pattern. The SP interference pattern provides better resolution than what can be realizes using either laser interference or any other conventional optical imaging methods at the same frequency.

As will become apparent below, SP interference patterns can be applied to achieve high resolution nanolithography. In some implementations, instead of using a coupling grating, a single sharp edge or slit may be used to excite SPs. Other medium configurations with other types of surface features may also be used. Where a film with sharp edge or slit is used, the diffracted light from the edge or slit gains very broad band of wave vectors; the interface will automatically select the components with matched wave vector, and support its propagation on the surface. Because this is not a resonant process as in the case of a grating, only a small portion of the light will couple to SPs. However, the contrast of the SP interference fringes will not be affected if only SPs, but not any other forms of light, exist at the surface.

Figure 4:
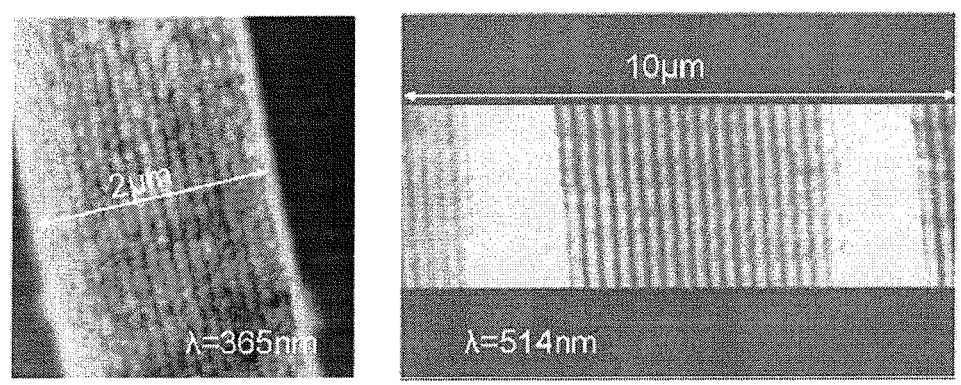
FIG. 4 includes images of SP interference patterns.

FIG. 4 shows experimental results of SP interference patterns formed on top of a metallic stripe. Depending on the desired working wavelength, either Al or Ag film may be used to support the SPs. In both cases, uniform SP interference patterns have been observed with high resolution. For instance, the interference pattern on left image of FIG. 4 shows periodicity of about 125 nm which is about ⅓ of the working wavelength in free space. This agrees well with the simulation results shown in FIG. 3 even though a single edge is used for SP excitation. The very small difference of the periodicity comes from the thin layer of the photo-resist used in the experiment which effectively reduced the refractive index of the dielectric layers.

Plasmionic Structured Illumination Microscopy

Figure 5:
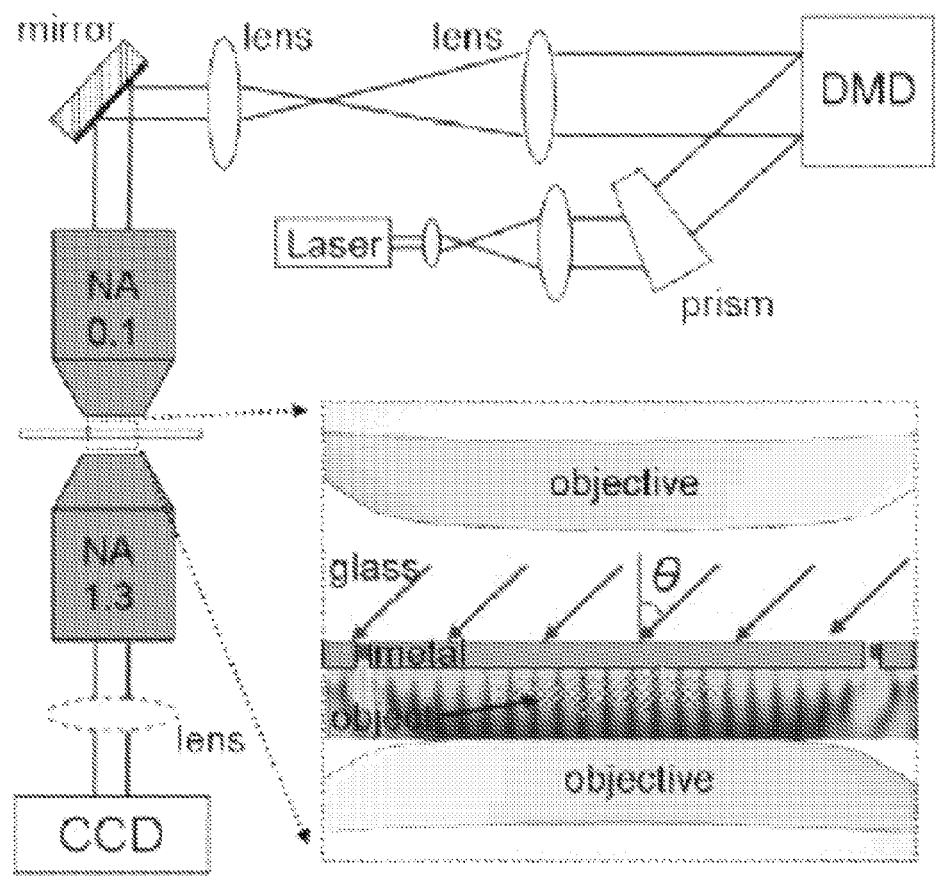
FIG. 5 is a schematic diagram of a system to perform microscopy using surface plasmons.

With reference to FIG. 5 a schematic diagram of a microscopy system 100 to perform microscopy using surface plasmons generated through optical excitation is shown. The system 100 includes an optical source 110 to generate optical energy that is subsequently modulated by a modulator 120 and directed towards a medium 150 that includes one or more surface features (e.g., slits, grating arrangements, etc.). The medium properties and the surface features defined on the medium are configured to produce a particular surface plasmon interference pattern in response to application of optical radiation, having its own corresponding controllable interference pattern and/or applied at a particular controllable incident angle. Thus, and as will be described in greater detail below, the SP interference pattern produced by the medium 150 is based on one or more of the nature of the medium 150, the configuration of surface features defined on the medium, the radiation interference pattern irradiating the medium and/or the angle of incident at which the optical radiation is applied to the medium 150.

In some implementations, the medium may be a metal/dielectric interface (e.g., plate or sheet) that includes slits, gratings and/or other surface features incorporated into a metal layer to convert free space light (the excitation optical radiation) into surface-confined plasmons. The type of metal and excitation light wavelength are generally chosen, and the surface features are dimensioned, shaped and/or configured, so the plasmons from each slit and/or grating (or any other surface feature) may overlap to create an interference pattern with periodicity that is generally shorter than the wavelength of the excitation light. Generally, the medium's material (e.g., a metal) with its associated properties (e.g., dielectric indices, conductivity, etc.) is first selected, followed by formation of the medium's geometry (dimensions, formation of surface features, etc.) The material's selection may largely be determined by a combined consideration of the intrinsic material properties in terms of practical fabrication quality as well as complexity. For example, silver (Ag) is considered to be a suitable material for plasmonic applications requiring radiation having wavelengths in the visible frequency, while gold (Au) and aluminum (Al) are generally considered to be suitable for applications involving radiation with wavelengths in the near infrared or ultraviolet regions, respectively. In the implementations depicted in FIG. 5 the medium is structured as periodic two-dimensional (2D) slit array (FIG. 5 illustrates a cross-sectional view of the medium's geometry).

Characteristics of the plasmon interference patterns are therefore controlled by configuring the medium in some predetermined manner (i.e., selecting the medium material and geometry). Additionally, the plasmon interference patterns may further be controlled by controlling the polarization, angle of incidence of the excitation light relative to the metal/dielectric interface, and the interference patterns of the excitation energy.

In some implementations, other types of excitations energies may be used to excite (and thus generate) SP interference patterns. For example, electron beams, produced by an electron beam source, may be directed to a metal film to excite SP interference patterns.

Thus, in response to a sequence of two or more medium excitation patterns having associated interference patterns, resulting corresponding two or more surface plasmon interference patterns are excited in the medium. To achieve resulting varying surface plasmon interference patterns, the excitation energy incident at the medium may be such that it causes different SP interference patterns to be generated. For example, the incident light at one instance may be applied at a different incident angle and/or may have a different polarization than the incident angle and/or polarization of light applied at a subsequent time instance to thus cause SP interference patterns with corresponding different phases. In another example, the incident excitation light at one instance may include an interference pattern that is different from the interference pattern of the applied excitation light at a subsequent time instance.

Figure 6:
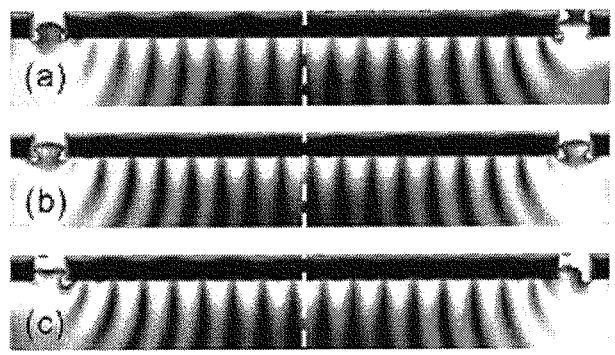
FIG. 6 includes images showing the resultant stimulated E field distributions on a sliver film in response to optical radiation applied at varying incidental angles.

For example, and with reference to FIG. 6, images showing the resultant stimulated E field distributions on a sliver film in response to optical radiation applied at varying incidental angles are shown. The SP interference patterns shown in images (a), (b) and (c) resulted from application of optical radiation with a wavelength of 514 nm on a silver film including two identical slits with a width of 250 nm located at a distance of 4 µm from each other. The optical radiation used in the illustration of FIG. 6 was applied at incidental angles (relative to the normal of the surface of the silver film) of $\theta=0°$ (resulting in the pattern shown in image (a)), $\theta=2.45°$ (resulting in the pattern shown in image (b)), and $\theta=4.9°$ (resulting in the pattern of image (c)). As indicated by the position of the fringe closest to the dashed line in each of the images of FIG. 6, applying optical radiation interference pattern at different incidental angles results in surface plasmon interference patterns having different phases (and thus different patterns that can be used to obtain a high resolution reconstructed image).

When converting the free space light into SP and forming interference patterns, it is generally required that only the high resolution SP interference pattern are applied (illuminate) the specimen while shielding the free space light so that it does not illuminate the specimen. In order to substantially eliminate background light, i.e., the directional transmission of the free space light, an optically thick metallic film should be used.

In some implementations, the structure comprising the medium 150 may be configured as a removable "plasmonic structure insert" that may be easily inserted into and removed from a system such as the system 100. Such a removable structure is configured to convert free space light into surface plasmons and create plasmonic interference patterns in the manner described in relation to medium 150, and may be constituted by at least one metal/dielectric stack, e.g., optically thick metal film on glass, or metal/dielectric multilayer on glass, in which the metal film includes an arrangement of one or more surface features such as slits or gratings that, when illuminated by optical radiation, result in the formation of predictable interference patterns. Thus, in implementations of a system such as a system 100, a user may use with the system one of several available plasmonic structure inserts that each corresponds to different interference patterns generated in response to application of optical radiation on the respective insert. The choice of which plasmonic structure insert to use would thus depend on the nature of the particular interference patterns required for the imaging of the specimen in question.

To achieve image reconstruction, multiple measurements with relative phase-shift between the object and the illumination patterns should be taken. In a conventional SIM, the illumination light pattern is generally realized by translating or rotating a physical grid that is placed at a conjugate plane of the object plane. In the case of PSIM, efforts are made to avoid such mechanical translations of a bulky mask in order to improve the image acquisition and reconstruction speed. As noted, the phases of the SP waves may be tuned by the incident angle of an excitation optical radiation (e.g., a laser beam modulated by the modulator 120), leading to a realization of focus tuning for a plasmonic lens. When a tilted excitation laser beam hits on the metallic structure, the light at the two slits possess different phases. The phase difference will be transferred to the surface plasmon waves after a scattering process of the slit resulting in lateral translation of the SP interference pattern. As a consequence, the phase-shift control of the interference pattern can be simplified by controlling the phase difference when the excitation light at the two slits, i.e., the incident angle of the excitation laser beam. As will be described in greater detail below, in some implementations, the incident angle control may be realized by controlling a fringe pattern on a digital mirror device (DMD).

Figure 7:
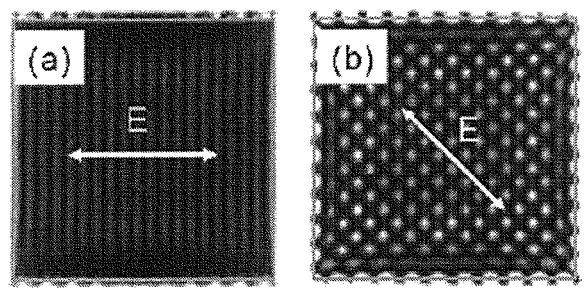
FIG. 7 includes images of simulation results showing how polarization is used to control SP interference patterns over a square plasmonic structure.

The interference fringes have to be aligned along at least two directions, vertical and horizontal for instance, to obtain enough two dimensional information to form a high quality image. The orientation of the SP interference patterns may be controlled by a pre-designed shape of the slits with a combination of the polarization selection for the excitation light. For example, FIG. 7 include simulation results showing how polarization is used to control SP interference pattern over a square plasmonic structure. The white arrows in FIGS. 7a and 7b represent the polarization direction of the excitation light. Thus, in the simulation example of FIG. 7, two alternatives are implemented. In the first alternative, depicted in FIG. 7a, one polarization is selected, and subsequently multiple images with various incident angles are taken along the same direction. This is followed by repeating the same process at the other direction. In the second alternative, depicted in FIG. 7b, a fixed 45° polarization excitation is used, with the capture of multiple images with various incident angles taken along both vertical and horizontal directions. The square plasmonic structure shown in FIG. 7 is one specific example. In some implementations, other plasmonic structures may be used, including hexagonal plasmonic structures that are able to generate interference fringes along three directions with 120° degrees apart.

Turning back to FIG. 5, in some implementations, the system 100 uses a dual, opposing objectives microscope configuration, where the excitation light beam is steered and controlled through one objective while the specimen is observed and its image collected through another objective. Thus, a top objective 160 couples the optical radiation directed from the modulator 120 to the medium 150. The optical radiation illuminates the medium 150 at its top surface 152, and excites a resulting interference pattern. As noted, the resulting SP interference pattern has a smaller wavelength than the wavelength of the excitation radiation.

The SP interference pattern is applied/directed to the specimen (sample) 170 to cause a resulting image (e.g., an optical image) of the specimen to be generated. In some embodiments, where the sample include fluorescent dyes to enable fluorescent microscopy, the SP interference patterns cause the fluorescent dyes to emit optical radiation responsive to the EM field corresponding to the generated SP interference pattern. The optical image resulting from the fluorescent dyes reacting to the presence of the particular SP interference pattern can then be used, as will become apparent below, to reconstruct an image of the specimen. In some embodiments, optical images resulting from the SP interference patterns that are used to investigate the specimen are achieved from the scattering effect of evanescent waves of the SP interference patterns interacting with the specimen.

The image resulting from the SP interference patterns used to investigate the specimen is coupled to an objective 162 and is then captured (e.g., optionally via one or more optical elements, such as a lens 164, when the image is an optical image) by a capturing device 180 such as, for example, a charge-coupled device (CCD) camera 180. Suitable CCD cameras that may be used include, for example, a Phantom Miro CCD with an imaging speed of 2200 frames/second at a resolution of 512×512. Other types of capturing devices may also be used. The objectives 160 and 162 used with the system 100 may include an objective with a relatively low numerical aperture (NA), e.g., 0.1-0.3 (or even lower), to direct the light onto the specimen, and an objective to gather the light received from the specimen observed (i.e., corresponding to the objective 162) with a relatively large numerical aperture, e.g., 1.2-1.4, although objectives with any NA may be used. In some implementations, the objectives may be replaced with common optical lenses.

Accordingly, the capturing device 180 captures images resulting from the sequences of two or more surface plasmon interference patterns applied to the specimen 170. The captured images include high frequency information contained in the moiré fringes of the captured images. The captured images are then forwarded to a processing module 190 that receives the captured images of the specimen, and based on the captured images, the processing module generates a reconstructed image of the specimen. Reconstruction of the images based on the sequence of two or more captured images which include the high frequency moiré fringes information may be performed by, for example, obtaining the Fourier transform of the captured images, and shifting the Fourier-transformed images in a corresponding direction and distance that are based on the illumination patterns that resulted in the images whose Fourier representations are being shifted. Multiple relocated Fourier-transformed images are subsequently combined into an extended Fourier image. The reconstructed final high resolution image is obtained by performing an inversed Fourier transform to the extended Fourier image. Additional examples of procedures to reconstruct the image from the captured images are provided, for example, in M. G. L. Gustafsson, "Surpassing the lateral resolution limit by a factor of two using structured illumination microscopy," *J. Microsc.* 198, 82-87, 2000, the content of which is hereby incorporated by reference in its entirety.

The processing module 190 may be implemented using one or more processor-based devices that may include a computer and/or other types of processor-based devices suitable for multiple applications. Such devices can include volatile and non-volatile memory elements, and peripheral devices to enable input/output functionality. Such peripheral devices include, for example, a CD-ROM drive and/or flash drive, or a network connection, for downloading related content, for example, the image data obtained from the illumination of the specimen using generated surface plasmon interference patterns, and computer instructions to generate a reconstructed image of the specimen from such image data. Such peripheral devices may also be used for downloading software containing computer instructions to enable general operation of the respective system/device. In some implementations, the various processing module operations, e.g., to generate the reconstructed image, may also be performed, for example, by using special purpose logic circuitry, e.g., an FPGA (field programmable gate array) or an ASIC (application-specific integrated circuit).

As noted, in some implementations, surface plasmons at the surface 152 of the medium 150 may be excited using optical radiation, originating by the source 110 and modulated by the modulator 120, that is applied to the medium as a sequence of two or more optical interference patterns, with at least one of the two or more sequential optical interference patterns being different (e.g., different patterns and/or different incident angles) from another of the two or more sequential optical interference patterns. With continued reference to FIG. 5, in some implementations, the optical source 110 may include one or more of a laser source, an incoherent lamp which may be equipped with an optical filter to provide optical energy with a narrower optical band (or even provide a resultant optical radiation with a particular wavelength), etc. In the implementation depicted in FIG. 5, the optical source 110 is a laser source, such as, for example, a laser source generating optical radiation with wavelengths in the visible range of the EM spectrum (e.g., optical radiation with a wavelength of 532 nm). Examples of suitable laser sources may include Gas lasers, diode lasers, diode-pumped solid-state lasers, fiber-based lasers, pulsed lasers or tunable lasers, etc. Alternatively and/or additionally, in some implementations a laser source that generates radiation outside the visible range may be used in conjunction with frequency multiplier devices (frequency converter devices) devices, e.g., KTP crystals, to produce laser radiation in the visible range. Examples of such laser-generating configurations include a frequency multiplier used in conjunction with one of Nd:YAG laser operating in the infrared spectrum, for example, at a wavelength of 1064 and Nd:YLF laser system, an Yb:YAG laser system, a CO2 laser system, laser systems emitting laser radiation with wavelengths in the UV range, laser diodes (which may be arranged in a diode array), etc.

As noted herein, in some implementations, other types of energy that may be illuminated on the medium to excite surface plasmons interference patterns may be used. For example, the excitation energy may be in the form of electron beam generated by an electron gun.

As further noted herein, the optical energy generated by the source 110 is directed to a modulator 120 configured to modulate the optical energy it receives to produce optical radiation with a particularly controlled patterns and/or to cause optical energy that is directed to the medium 150 (via, for example, an arrangement of optical elements, including an optical element such as the objective 160) to be applied at particular controllable angles. The optical energy generated by the source 110 may be directed to the modulator 120 using an optical arrangement 112 comprising one or more optical components such as lenses (e.g., lens 114), mirrors, space light modulators, prisms (e.g., prism 116), that are used to steer, split or otherwise control or modify the optical beam directed to the modulator 120. The optical arrangement 112 defines the path through which the optical energy generated by the source 110 may travel to reach the modulator 120. Modulated optical radiation patterns formed using the modulator 120 correspond to the plurality of differing optical patterns illuminated on the medium In some implementations, the modulator 120 may include, for example, a digital mirror device (DDM), which is a device that includes on its surface a large number of microscopic mirrors (e.g., mirrors constructed from aluminum). The mirrors can be individually rotated to an On state, in which light from the source 110 is reflected towards the arrangement of microscope's objectives and specimen, or to an Off state, in which the received light is directed elsewhere. In some implementations, electrodes for each of the individual mirrors of the DDM are used to control the position of the mirror by electrostatic attraction.

As further shown in FIG. 5, a modulator controller 122 is electrically coupled to the modulator 120 to control the operation of the modulator 120. For example, in the implementation of FIG. 5, the modulator controller is a DMD controller configured to control the movement/positions of the mirrors comprising the DMD to thus modulate the received light in such a way so to consequently generate the required sequence of surface plasmon interference patterns used to obtain a high resolution reconstructed image. The modulator controller 122 generates and transmits electrical signals to control the mirrors so that light reflected from the DMD has patterns (e.g., interference patterns) to cause a resultant sequence of surface plasmons interference patterns to be formed. In some implementations, the controller 122 may be implemented using one or more processor-based devices that may be similar to the processor-based device used to implement the processing module 190 used to reconstruct the sequences of images obtained from the sequence of surface plasmon interference patterns. Thus, such one or more processor-based devices may include a computer and/or other types of processor-based devices suitable for multiple applications. Such devices can include volatile and non-volatile memory elements, and peripheral devices to enable input/output functionality. Such peripheral devices include, for example, a CD-ROM drive and/or flash drive, or a network connection, for downloading related content, for example, data representative of optical interference patterns for the optical energy that is to be modulated by the modulator 120, and computer instructions to cause the processor-based device to control the modulator (e.g., control the individual mirrors of the DMD). Such peripheral devices may also be used for downloading software containing computer instructions to enable general operation of the respective system/device. In some implementations, the various modulator control operations, e.g., to generate control signals to control individual mirrors of a DMD-based modulator device, may also be performed, for example, by using special purpose logic circuitry, e.g., an FPGA (field programmable gate array) or an ASIC (application-specific integrated circuit). In some implementations, the controller 122 may be implemented using the same hardware used to implement the processing module 190.

Figure 8:
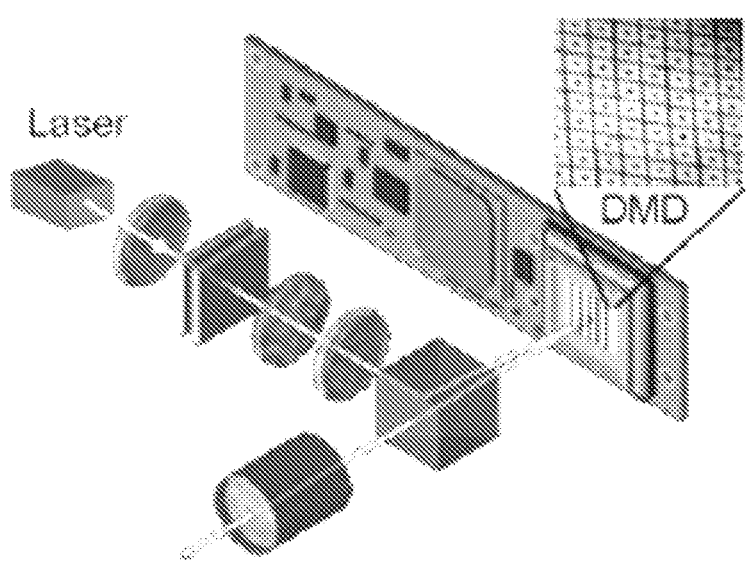
FIG. 8 is a schematic diagram of an arrangement including a laser source and a digital mirror device.

With reference to FIG. 8, a schematic diagram showing the arrangement of the laser source 110, a DMD-based modulator 120', and an optical arrangement 112' to direct the optical radiation generated by the source 110 to the DMD-based modulator 120'. The schematic diagram provides a magnified view of a portion of the DMD, illustrating a portion of the array of micro-mirrors used to modulate the optical radiation directed to the mirror by the optical arrangement 112. Thus, as shown, a collimated laser beam is reflected by the DMD 120' based, for example, on computer controlled patterns (stored, for example, on a storage device of the modulator controller 122) at ultra fast speed. The controlled dynamic patterns are coupled to the objective 160 by an optical arrangement 130 (shown at FIG. 5) to excite surface plasmon patterns, in the metallic structure, that are applied to the specimen and cause resulting images to be generated (e.g., fluorescent dyes interacting with the SP interference patterns to cause the dyes to emit optical radiation responsive to the particular SP interference pattern excited in the medium, scattering effect from the interaction of the specimen with evanescent waves of the SP interference patterns, etc.).

In some implementations, other types of modulators may be used to modulate the optical energy received. Other types of suitable modulators include, for example, an electro-optical modulator, an acoustic-optical modulator, a liquid crystal modulator, an optomechanical modulator, etc. The liquid crystal modulator, for example, comprises an array of cells that are generally controlled by a computer (or equivalent). Light from a light source is steered to the modulator and received at a receiving surface, whereupon the incident light travels through those cells that were controlled/actuated to enable transmission. The transmission through the liquid crystal modulator is guided to the objective 160. Electro-optical modulators, acoustic-optical modulators, and optomechanical modulators use different effects (electro-optical effect, acousto-optical effect, mechanical movement of a grating or mirror) to change the propagation direction of an incident light beam through such modulators. If a light steering model is used to guide the transmission light to the objective 160, the incident angle of the illumination light to the plasmonic structure can then be controlled by the modulator.

In some implementations, the radiation source, the modulator and the medium configured to generate the surface plasmons may be combined into a single integrated plasmonic chip. For example, such an integrated chip may include a LED chip to provide the optical radiation, and a plasmonic structure positioned adjacent to the LED chip. Such implementations may utilize an electrical pumping method to excite the surface plasmons. Additionally, in such integrated plasmonic chip implementations, the chip can be relatively easily inserted and removed into a microscope apparatus (e.g., the chip can be placed above the specimen).

Figure 9:
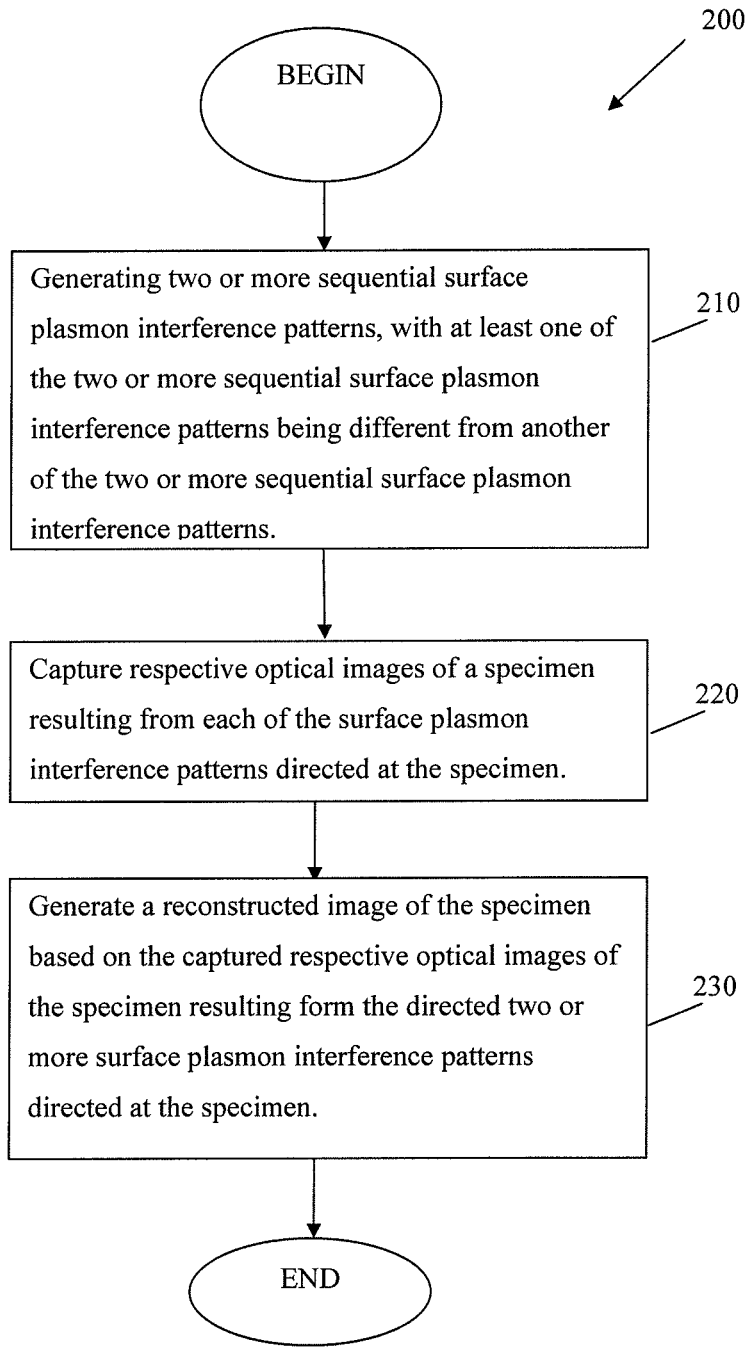
FIG. 9 is a flowchart of a procedure in which illumination of a specimen is implemented using interference patterns generated by surface plasmons.

Referring to FIG. 9, a flowchart of a procedure 200 based on structured illumination in which the illumination of a specimen is provided by interference patterns generated by surface plasmons is shown. To obtain a high resolution image, two or more sequential surface plasmon (SP) interference patterns are generated 210, with at least one of the two or more sequential surface plasmon interference patterns being different from another of the two or more sequential surface plasmon interference patterns. In some implementations, the two or more sequential SP interference patterns are generated by directing energy from an energy source to a modulator that controllably modulates the energy into one or more pre-determined interference patterns that are then applied to a medium such as a metal/dielectric interface with surface features (e.g., slits, grating, etc.) defined thereon. To generate the sequence of SP interference patterns, where at least one pattern is different from another pattern (so that different images of the sample can be captured), the incident energy applied to the medium may be applied at different incident angle, at different polarization and/or the incident energy may correspond to different sequential interference patterns. In some implementations, the energy applied may be optical radiation modulated by a digital mirror device. In some implementations, other types of incident energy may be used, for example, electron beams.

The generated SP interference patterns, which have a wavelength that is smaller than the wavelength of the radiation that was used to illuminate the medium, are applied to the specimen. The respective images resulting from the SP interference patterns applied to the specimen are captured 220 by a capturing device such as a CCD camera used to capture optical images. A sequence of captured images resulting from the sequence of the SP interference pattern is then used to reconstruct 230 the image of the specimen.

Figure 10:
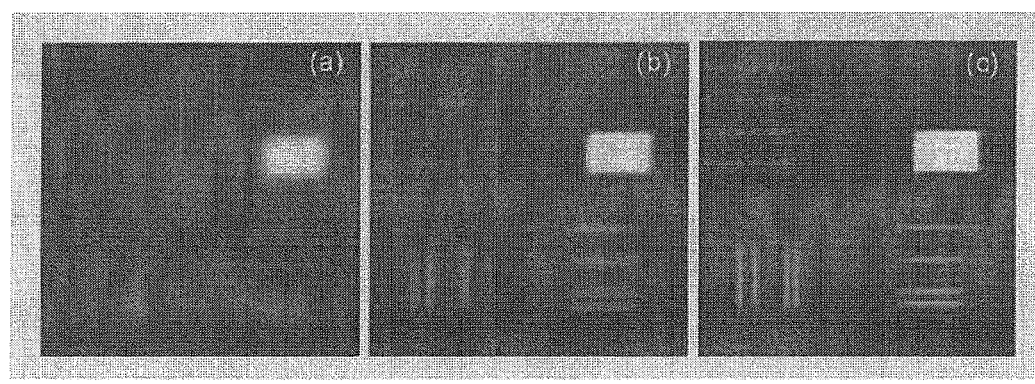
FIG. 10 includes imaging results based on numerical simulations of various imaging techniques.

To provide more insight about how the final PSIM imaging looks like and how it differs from conventional optical microscope and conventional SIM, numerical simulations of various techniques were performed, with the results being presented in FIG. 10. FIG. 10$a$ shows the imaging results of a directional image obtained through conventional optical microscope. FIG. 10($b$) is an image reconstructed through common SIM, with $k_{str}=k_{obs}$. FIG. 10($c$) is an image reconstructed through PSIM technique, in which $k_{str}=2k_{obs}$. The simulation results shown in FIG. 10 were performed based on the assumption that the illumination patterns applied to the specimen being observed were vertical and horizontal. As illustrated in the simulation results of FIG. 10, the simulation results for the PSIM techniques demonstrated significant resolution improvement compared with conventional optical microscopy and SIM techniques.

An important aspect of the implementation of a PSIM-based system is the achievable imaging speed. The imaging speed is generally predicated on two factors: (1) the illumination pattern refreshing rate, and (2) the image acquisition rate. The image reconstruction process can be done offline and therefore it does not significantly impact the performance of the system. As noted, a suitable commercialized imaging CCD camera is the Phantom Miro camera, having an imaging speed that is able to reach 2200 frames/second at full resolution (512×512). The speed of the camera may be increased by selecting a smaller area of interest with respect to which images are captured. In implementations in which images are reconstructed using six measurements (two perpendicular pattern orientations and three measurements with different phases for each orientation), the speed for PSIM implementation may be limited by the image acquisition, e.g., about 400 frames/second in some experiments. This speed is generally considered to be adequate for most real-time imaging applications.

In conventional implementations of SIM-based imaging system, the bottleneck for image acquisition and reconstruction generally was the speed at which the illumination light could be modulated. In the past, such function was mainly implemented through mechanical translation and rotation of a physical grid mask, which resulted in relatively slow modulation speed, and thus the possibility for dynamic imaging was not considered to be feasible.

As described herein, a light illumination arrangement that includes a light source and a modulator, similar to the light illumination arrangement depicted in FIGS. 5 and 8, may be used. Such a light illumination arrangement may include a digital mirror device (DMD) to control and modulate the illumination light at ultra-fast speeds. The light modulated and reflected from the DMD is guided to a microscope to shrink the illumination pattern to thus control the incident angle at desired microscales. Initial testing of an apparatus similar to the one depicted in FIGS. 5 and 8 achieved a 60 Hz frame rate by using such a common DMD in a commercialized projector. However, this frame rate can be increased to 13,000 Hz by removing or suppressing the DMD's complicated color regulation and gray scale control functionalities since those functionalities are not required in the implementation of PSIM-based imaging techniques. A frame rate of 13,000 Hz is generally sufficient to match up with the imaging CCD camera speed.

As further noted herein, the incident angle of the laser beam is controlled by sending different binary fringe images with various periods and orientations. The light patterns directed by the modulator (e.g., the DMD) is coupled into an objective through a set of optical lenses and also, optionally, spatial filters.

It is worth noting that the optical signal level of the specimen is also an important factor affecting the final imaging speed in PSIM implementations. In order to get enough photons for an image with good signal to noise ratio, certain exposure time is required during the image acquisition process that ultimately will also affect the speed. In principle, a strong excitation laser is always helpful for this purpose but may generate addition problems, such as sample damage and heat related distortions. As an alternative approach, consideration may also be given to implementations that include the use of an electro-optical modulator (EOM) to control the beam incident angle. The idea is to control a light beam position at the back focus plane of the illumination objective by regulating an input voltage of an EOM. One advantage for this approach is that it is a one-bit beam modulation rather than a multi-bit pattern modulation as in the case of DMD. Therefore, it is easier to raise the imaging speed, under these circumstances, up to MHz.

As noted, the PSIM-based implementations described herein result in relatively high resolution reconstructed images. The theoretical limit of PSIM in terms of both spatial and temporal resolution can be determined, and an estimate can be computed of how far a practical system can reach those two aspects.

As described, the imaging speed of the PSIM may be fundamentally limited by three factors: the number of photons radiated from the specimen, the capturing device's imaging speed (e.g., the CCD's imaging speed), and the illumination speed. All these factors are either predefined by the nature of the specimen and/or the technology. The spatial resolution limit, which includes extensive plasmonic structure design, may be determined as follows. As shown in FIG. 1d, the accessible spatial frequency for SIM (and thus its resolution) is determined based on the relationship $k_{obs}+k_{str}$. The factor $k_{obs}$ is determined by the conventional far-field detection optics (for example, $k_{obs} \leq 1.3 k_0$ in the case of an objective with an NA=1.3, which is the NA of the objective used in the implementation depicted in FIG. 5). The factor $k_{str}$ is generally limited by the wavevector of SPs. In principle, the SP wavevector can be designed to reach very high values by selecting appropriate materials, metal film thickness, working wavelength, and the geometry of the coupling elements (e.g., the slit width and distance between slits). In addition, the single layer of metal film can also be replaced by a composite material comprising much thinner metal/dielectric multilayer structures for more opportunities to engineer the SP modes and the SP interference patterns. Experiment results have shown that multilayer stacks can in fact achieve good results. Strategies may also be implemented to develop and optimize the plasmonic structure for better performance of the PSIM by taking into account all the aforementioned possibilities.

The practical limitation has to consider the imperfections of the system. For instance, the surface roughness of the medium introduced in the fabrication process will set additional limitation on the spatial resolution. A model may be used to incorporate such imperfections into the final resolution. For example, the surface roughness can be measured using atomic force microscope and the model may thus be adapted to include equivalent materials loss parameters.

To illustrate the potential and possible uses of the systems and methods described herein, the following examples are provided. One example relates to two-dimensional Brownian motion imaging. This system could be either a physical system comprising metallic or fluorescent particles in a liquid, or biological system with moving objects on a living cell membrane. It is expected that using such a highly dynamic system, a PSIM-based implementation will be able to monitor dynamic events with enhanced resolution. Moreover, the PSIM-based implementation may be used for both scattering and fluorescent imaging. Samples with biological significance may be used as well.

Another example relates to neurotransmitter imaging. The complex functionalities of the neuron network systems are fundamentally accomplished by the communications between neurons, i.e., the movement of chemicals across a small gap called the synapse. Chemicals, called neurotransmitters, are released in a form of vesicles from one neuron at the presynaptic nerve terminal, then cross the synapse where they may be accepted by the next neuron at a specialized site called a receptor. The kinetics of the vesicle have been considered an important foundation for higher level neuro-activities. Because the size of the vesicles is typically on the scale of a few tens of nanometers, most of the current high-resolution studies are carried out by scanning electron microscope (SEM). Although SEM-based system may provide good spatial resolution, to observe interactions such as those occurring in a neuron network system, the samples have to be frozen and thus the images obtained pertain to images at a "fixed time". The kinetics study of the vesicles is generally considered to be challenging with SEM and/or any other conventional imaging tools. However, it is expected that imaging using PSIM-based systems may enable to study such interactions at a level of detail that cannot be achieved with SEM and/or other imaging systems.

High Speed Laser Interference Structure Illumination Microscopy

Figure 11:
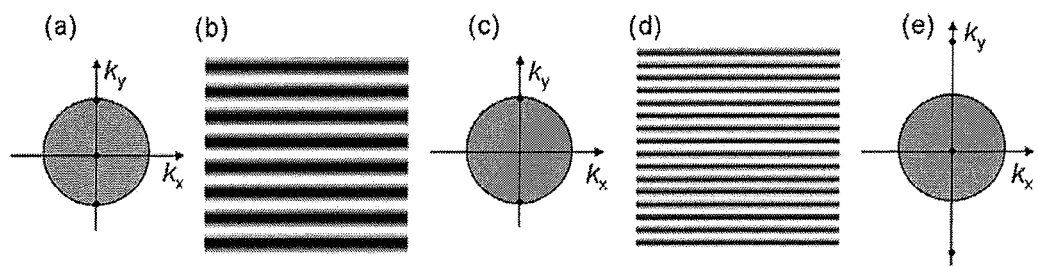
FIG. 11 includes diagrams showing the principle used to achieve high-speed laser interference SIM through removal of a zero-order light component.

As noted, also described herein is a system and method that includes a system to generate, using an optical source and a controllable modulator to modulate generated optical radiation, two or more sequential optical interference patterns with at least one of the patterns being different from another of the two or more interference patterns, and a beam stopper to remove from each of the generated optical interference patterns the corresponding zero-order diffraction light component and/or low-order components FIG. 11 shows the underlying principle employed in the implementations described herein to achieve high speed laser interference SIM by removing the zero-order component of each of the optical interference patterns applied to a specimen to be observed. FIGS. 11(a) and (b) corresponds to conventional illumination method in which the zero-order (also referred to as 0-order) component of an illumination pattern (e.g., generated from one or more optical sources) is not removed. As shown, the three components present in the Fourier space depicted in FIG. 11(a) corresponds to interference fringes in real space depicted in FIG. 11(b). Under these circumstances, the fringe resolution is limited by $\lambda/NA$, where NA is the numerical aperture of the objective used to direct illumination to the specimen. In contrast, by blocking the zero-order in the back focus plane of an objective (e.g., by placing an aperture at a conjugate plane), the final illumination k vector is able to go beyond the NA. Specifically, $k_{str}$ may be able to go up to $2NA \times k_0$ (see FIG. 11(e)). This is because only the intensity modulation needs to be considered in, for example, fluorescent microscopy. Thus, Fourier filtering of the zero-order component provides a way to double the k vector of the illumination light.

Figure 12:
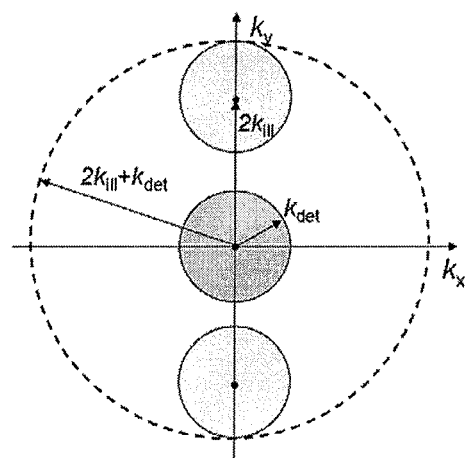
FIG. 12 is a diagram illustrating the Fourier space resulting from a SIM procedure in which zero-order components are removed.

If we apply this illumination method to fluorescence microscopy, the accessible information in the Fourier space is shown by the dotted circle in FIG. 12. The shaded areas represent the information that can be obtained by using the finest illumination pattern along one direction. By changing the period and orientation of the illumination patterns, the complete information within the dotted circle can be collected. The resolution enhancement factor, compared with conventional fluorescence microscopy, can be expressed as:

$$F = \frac{2k_{ill} + k_{det}}{k_{det}} = 1 + 2\frac{\lambda_{det}}{\lambda_{ill}} \quad (1)$$

As one example, the ultimate resolution can be estimated using a common green fluorescent protein (GFP) in fluorescence microscopy. The illumination and detection wavelengths for GFP are 395 nanometers (nm) and 509 nm, respectively. By plugging these values into the Equation (1), the resolution enhancement factor F is computed to be approximately 3.57. For other fluorescent molecules or quantum dots, the F value can be even higher. If a total internal reflection fluorescence (TIRF) objective with NA=1.65 (e.g., using an Olympus APO100XO-HR-SP) is used, the smallest resolve feature size is about 43 nm.

The subject matter described herein may be applied to 3D imaging with multiple colors. The illumination can be operated at a smaller NA to ensure the penetration into the specimen like a cell. If the NA=1.3, the resolution estimated based on the above Equation (1) is approximately 55 nm.

Figure 13:
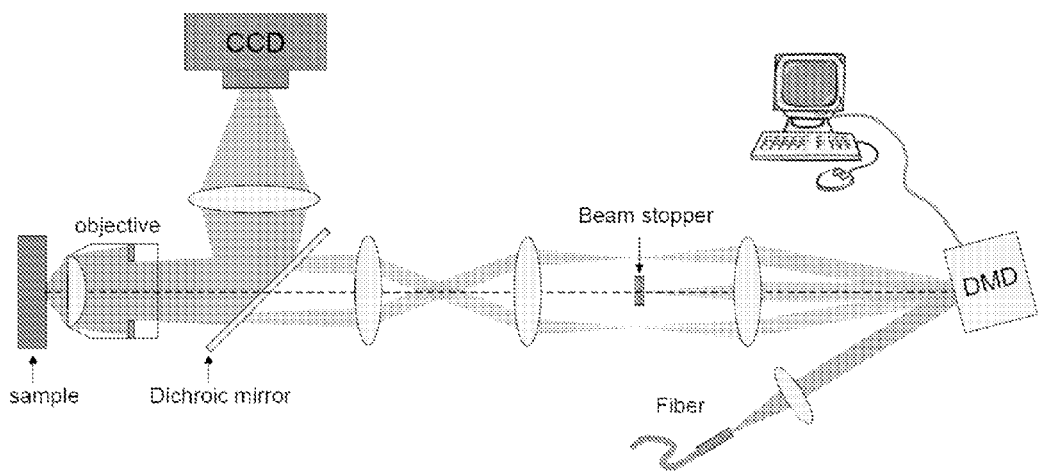
FIG. 13 is a schematic diagram of a system that includes a beam stopper to remove zero-order components of optical interference patterns.

With reference to FIG. 13, a schematic diagram of a system 300 that includes a beam stopper 330 to remove the 0-order component of optical interference patterns directed to illuminate a sample (specimen) is shown. The system 300 is configured to first cause collimated coherent light to be reflected by a modulator (e.g., digital mirror device, or DMD) with patterns controlled by, for example, a computer. Thus, the system 300 includes an optical source 310 and a modulator 320 to modulate the radiation provided by the optical source into interference patterns. The configuration including the optical source 310 and 320 may be similar, in some implementations, to the configuration used in relation to system 100 depicted in FIG. 5. Thus, the optical source 310 may include one or more of a laser source, an incoherent lamp which may be equipped with an optical filter to provide optical energy with a narrower optical band, etc. The source 310 may comprise a plurality of individual sources (e.g., multiple laser sources). In the implementation depicted in FIG. 13, the optical source 310 is a laser source, such as, for example, a laser source generating optical radiation with a wavelength in the visible range of the EM spectrum (e.g., optical radiation with a wavelength of 532 nm). Examples of suitable laser sources may include gas lasers, diode lasers, diode-pumped solid-state lasers, fiber-based lasers, pulsed lasers or tunable lasers. The 532 nm wavelength is an example, and radiation with different wavelengths may be used. Alternatively and/or additionally, in some implementations a laser source that generates radiation outside the visible range may be used in conjunction with frequency multiplier devices (frequency converter devices), e.g., KTP crystals, to produce laser radiation in the visible range. Examples of such laser-generating configurations include a frequency multiplier used in conjunction with one of Nd:YAG laser system, a Nd:YLF laser system, an Yb:YAG laser system, a $CO_2$ laser system, laser systems to generate radiation with wavelength in the UV range, one or more laser diodes (which may be arranged in a diode array), etc.

In some implementations, the energy generated by the one or more optical sources may be delivered via a waveguide 312 such as a fiber (e.g., an optical fiber, a laser fiber). The waveguide may include one or more optical fibers adapted to transmit the radiation (e.g., optical radiation) generated by the at least one optical source 310. Suitable waveguides to transmit optical radiation include, for example, glass or crystalline fibers, Sapphire fibers, Germanate glass fibers, a combination of Germanate glass fibers with Sapphire tip, hollow core fibers and/or any other suitable waveguide or radiation conduits to deliver laser energy. In some implementations, radiation couplers to couple radiation generated by the at least one optical source 310 to the waveguide 312 may be used.

The optical energy generated by the at least one optical source 310 is directed to a modulator 320 configured to modulate the optical energy it receives to produce optical radiation with particularly controlled patterns. The optical energy generated by the at least one source 310 may be directed to the modulator 320 using an optical arrangement 314 comprising one or more optical components such as lenses, mirrors, space light modulators (e.g., prisms) to steer, split or otherwise control or modify the optical beam directed to the modulator 320. The optical arrangement 314 defines the path through which the optical energy generated by the at least one source 310 may travel to reach the modulator 320.

In some implementations, the modulator 320 may include, for example, a digital mirror device (DMD), which, in some implementations, may be similar to the DMD 120 shown in FIG. 5. A modulator controller 322, which may be similar to the controller 122 of FIG. 5, is electrically coupled to the modulator 320 to control the operation of the modulator 320. For example, in the implementation of FIG. 13, the modulator controller is a DMD controller configured to control the movement/positions of the mirrors comprising the DMD to thus modulate the received light to generate a sequence of two or more optical interference patterns that can be directed to the specimen to implement the SIM method described herein. The modulator controller 322 generates and transmits electrical signals to control the mirrors so that light reflected from the DMD has patterns (e.g., interference patterns). In some implementations, the controller 322 may be implemented using one or more processor-based devices that may include a computer and/or other types of processor-based devices suitable for multiple applications. Such devices can include volatile and non-volatile memory elements, and peripheral devices to enable input/output functionality. Such peripheral devices include, for example, a CD-ROM drive and/or flash drive, or a network connection, for downloading related content, for example, data representative of optical interference patterns for the optical energy that is to be modulated by the modulator 320, and computer instructions to cause the processor-based device to control the modulator (e.g., control the individual mirrors of the DMD). Such peripheral devices may also be used for downloading software containing computer instructions to enable general operation of the respective system/device. In some implementations, the various modulator control operations, e.g., to generate control signals to control individual mirrors of a DMD-based modulator device, may also be performed, for example, by using special purpose logic circuitry, e.g., an FPGA (field programmable gate array) or an ASIC (application-specific integrated circuit).

With continued reference to FIG. 13, optical radiation modulated by the modulator 320 is directed, optionally via an optical arrangement that may include one or more optical components such as a lens 324, to a beam stopper 330 configured to block/remove the central zero-order light of the optical interference patterns directed from the modulator. In some implementations, the beam stopper is a material configured to block optical radiation. Such materials include, for example, opaque sheets or plates from appropriate materials (e.g., plastic, metal, etc.), dimensioned and/or structured to block low order light diffraction components, but not the high order components that are to be used in the illumination of the specimen Furthermore, in some implementations, the beam stopper may be configured to suppress/remove additional lower order light components from the interference pattern incident on the beam stopper 330. If a 1-D periodic pattern is sent to the modulator, the resultant illumination at the back focus plane of a microscope's objective 340 will include two spots appearing at the back focus plane of the objective 340. In some implementations, other high orders of the light may be blocked by the pupil of the microscope. This is equivalent to sending two plane waves with specific incident angle through the objective 340. The illumination pattern is thus a periodic interference fringes. 2-D periodic patterns may also be used.

It is to be noted that the period and the orientation of the fringes delivered into the objective 340 may, in some implementations, be entirely controlled by the controller 322. For example, the controller may control the modulator 320 to enable a series of pre-determined patterns to be generated from the optical radiation delivered from the at least one optical source 310 (the pre-determined interference patterns reflected from the modulator will be different from the interfered patterns reaching the objective 340 because the patterns generated via the modulator will include the zero-order components). The pre-determined patterns to be generated using the modulator 320 may repeat with some pre-determined periodicity.

The optical interference patterns from which the zero-order components have been removed are directed to the objective 340 via an optional optical arrangement that includes one or more optical components such as lenses (e.g., 332 and 334), one or more mirrors (e.g., a dichroic mirror 336 configured to enable transmission of the patterns incident on its surface 337 and to reflect optical radiation incident on its surface 338), etc. The sequence of optical radiations interference patterns missing their corresponding zero-order components (and/or other lower order components) is collected by the objective 340 and illuminated onto a sample 350. A capturing device 360, such as a CCD camera, which in some implementations may be synchronized with the modulator 320 (e.g., DMD) is used to capture the resultant images (e.g., florescent images) of the sample 350. Similar to the capture device 180 of FIG. 5, suitable CCD cameras that may be used in the implementations of FIG. 13 include, for example, a Phantom Miro CCD with an imaging speed of 2200 frames/second at a resolution of 512×512. Other types of capturing devices may also be used.

The capturing device 360 captures images resulting from the sequences of two or more optical interference patterns missing their respective zero-order component (and/or other lower order components). The captured images include high frequency information contained in the moiré fringes of the capture images. The captured images are then forwarded to a processing module 370, which may be similar to the processing module 190 of the system 100, to generate a reconstructed image of the sample (specimen) 350 based on the captured images. Here too, reconstruction of the images based on the sequence of two or more captured images which include high frequency moiré fringes information may be performed by, for example, obtaining the Fourier transform of the captured images, shifting the Fourier-transformed images in a corresponding direction and distance, combining the multiple relocated Fourier-transformed images into an extended Fourier image, and performing an inversed Fourier transform on the extended Fourier image to obtain a reconstructed image.

The ultra-high speed of the DMD (or other modulator used) will provide the required high refreshing rate during the image acquisition process.

The above-described configuration of the system 300 is one example of an implementation to realized a system that achieves high speed, high resolution imaging. Other implementations/configuration to generate a sequence of two or more optical interference patterns whose respective zero-order (and/or other lower order) optical components have been removed by a beam stopper may be used. For example, in some implementations, a light modulator to modulate the optical radiation from the source 310 may include, for example, a transmission-type, liquid crystal based spatial light modulator. Other high speed light modulators, such as acoustic-optical modulators and electro-optical modulators can also be adapted into the system.

In some implementations, currently existing commercial system may be modified to configure such systems to illuminate a sample with a sequence of two or more optical interference patterns whose zero-order and/or other lower order light components have been suppressed/removed. For example, in some implementations, a Carl Zeiss ApoTome instrument may be modified so as to replace its 1-D grid with a 2-D grid with either a square or hexagonal lattice. The grid projection control may be tunable along several directions which are aligned with the symmetry plane of the grid. Alternatively, the 1-D grid may be kept, and a rotational mechanism added to enable controlling the orientations of the 1-D grid.

Figure 14:
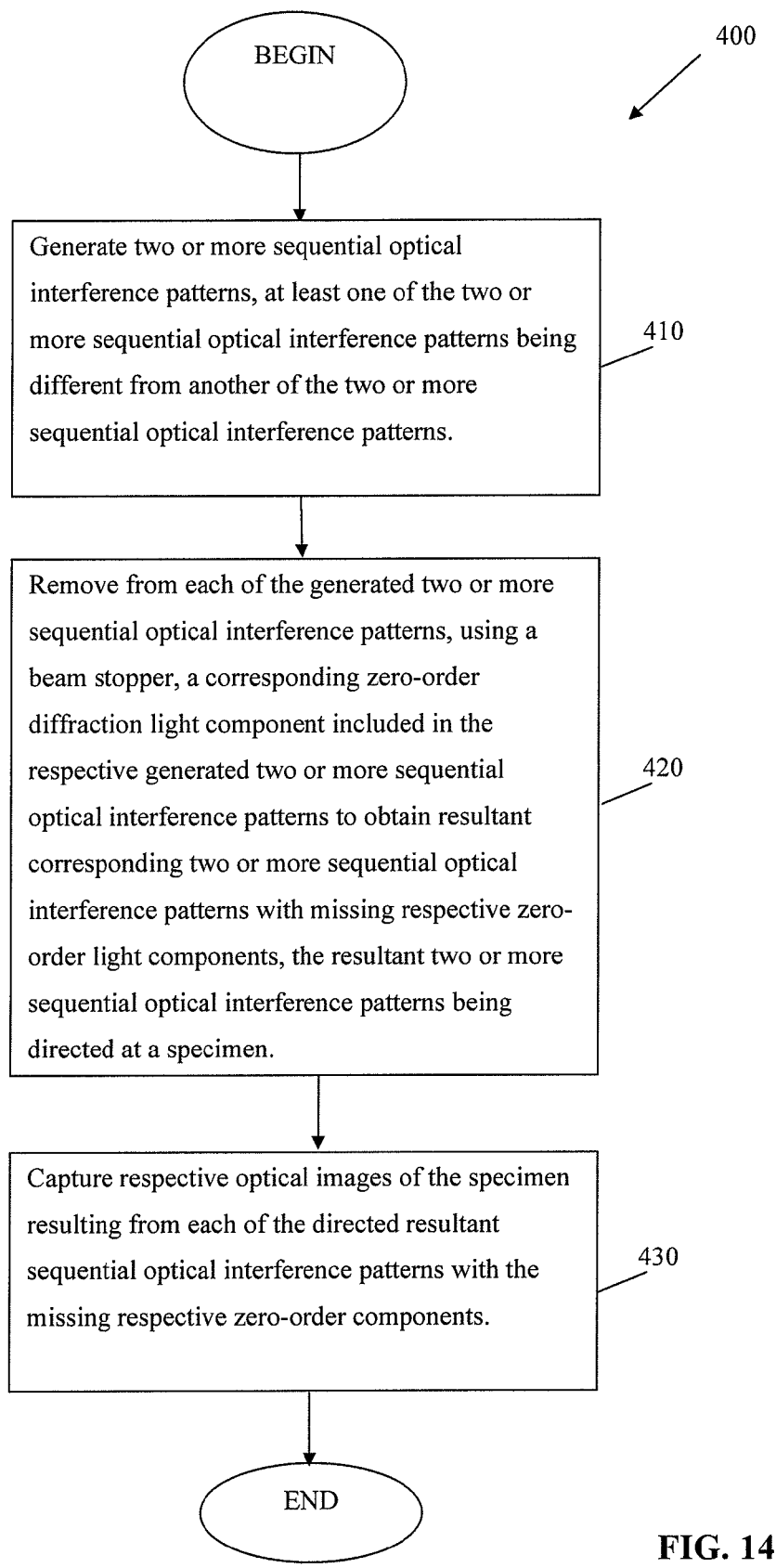
FIG. 14 is a flow chart of a procedure to illuminate a sample with interference patterns from which zero-order components have been removed.

With reference to FIG. 14, a flow chart of a procedure 400 based on structured illumination in which the illumination of a sample (specimen) is provided by interference patterns is shown. To obtain a high resolution image, two or more sequential optical interference patterns are generated 410, with at least one of the two or more sequential optical interference patterns being different from another of the two or more sequential optical interference patterns. In some implementations, the sequence of optical interference patterns is generated by directing optical radiation from at least one optical source to a modulator, such as a digital mirror device, electro-optical modulators, etc. In some implementations, the modulator modulates the received light to generate pre-determined interference patterns that are then directed to a microscope's objective to illuminate the sample.

Having generated the optical interference patterns, corresponding zero-order diffraction light components included in each of the respective generated two or more sequential optical interference are removed 420 using a beam stopper to obtain resultant corresponding two or more sequential optical interference patterns with missing respective zero-order light components, the resultant two or more sequential optical interference patterns being directed at a specimen.

In response to illumination of the sample by a sequence of interference patterns that include at least one interference pattern that is different from another interference pattern in the sequence, resultant optical images of the sample are obtained and captured 430 by a capturing device, such as, for example, a CCD camera. Based on the captured images, a high resolution image may be reconstructed.

Figure 15:
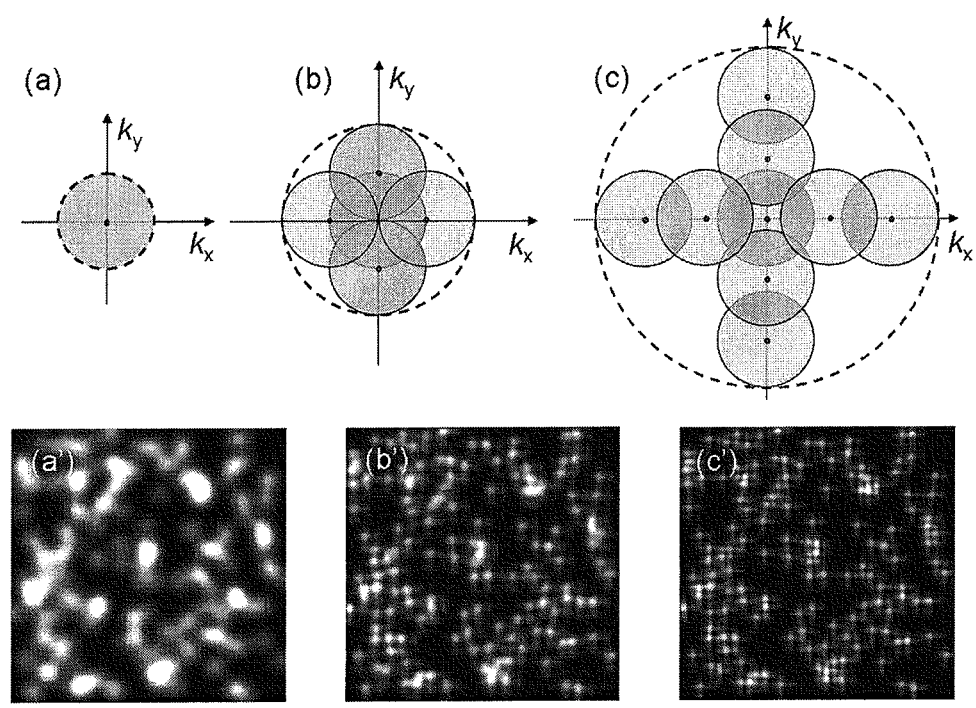
FIG. 15 includes imaging results based on numerical simulations of the various imaging techniques.

To provide more insight on the resolution enhancement achieved by the systems and methods described herein compared to conventional optical microscope and conventional SIM techniques, numerical simulations of the various techniques were performed, with the results being presented in FIG. 15. FIG. 15($a'$) shows a directional image obtained using a conventional optical microscope. FIG. 15($a$) is the corresponding Fourier space of the image of FIG. 15($a'$). FIG. 15($b'$) shows an image (of the same sample as that used in the case of FIG. 15($a'$)) reconstructed through application of a conventional SIM procedure, with $k_{ill} = k_{det}$. FIG. 15($b$) is the Fourier space corresponding to the image of FIG. 15($b'$). Lastly, FIG. 15($c'$) is an image reconstructed using the systems and methods described herein, and FIG. 15($c$) is the corresponding Fourier space for that image. It is to be noted that, as can be seen from FIG. 15($c$), more sampling images are generally needed to obtain the high-resolution reconstruction image. The reconstructed image of FIG. 15($c'$), for example, was obtained using 10 detected images with square lattice illumination patterns (different lattice constants and relative phases). However, increasing the number of sampling images by a factor of 10 (or even higher) will generally not affect high speed applications if a fast light illumination and detection mechanism is utilized.

It is further to be noted that in performing the simulations in relation to the images and diagrams of FIG. 15, it was assumed that the illumination patterns were vertical and horizontal. In practice, various other illumination patterns may be used, with the goal being that the illumination patterns cover as much area as possible in, for example, the dotted circle shown in FIG. 15($c$).

Thus, as shown from the images and diagrams of FIG. 15, the techniques/systems described herein achieve significant resolution improvement compared with both conventional optical microscopy and SIM.

Similar to the implementations described in relation to system 100, to provide a high imaging speed, a CCD camera, such as Phantom Miro, having an imaging speed that is able to reach 2200 frames/second at full resolution (512×512) may be used. The speed could be much higher is a smaller area of interest is selected. In implementations in which six measurements are performed to obtain images of the sample from which one reconstructed image frame is generated, the imaging system (e.g., the system 300) has an image acquisition rate of about 400 frames/second, which is generally adequate enough for most real-time imaging applications. Similar to the implementations described in relation to the systems depicted in FIGS. 5 and 8, in circumstances where a high-speed DMD is used to modulate the optical radiation to generate the optical interference patterns, the traditional bottleneck of using mechanical translation and rotation of a physical grid to modulate the optical radiation can be overcome. Thus, and as described above, in some implementation, the system 300 may include an arrangement, similar to the arrangement depicted in FIG. 8, of an optical source generating optical radiation that is modulated by DMD-based modulator. The illumination is controlled by sending different binary fringe images with various periods and orientations. The light patterns generated using the DMD are coupled into the objective 340 through a set of optical lenses and also with spatial filters.

It is also to be noted that the optical signal level of the object also plays a role affecting the final imaging speed. In order to get enough photons to obtain an image with good signal to noise ratio, certain exposure time is required during the image acquisition process that ultimately will also affect the speed. In principle, a strong excitation laser is always helpful for this purpose but may generate addition problems, such as sample damage and heat related distortions.

The subject matter described herein may enable deep sub-wavelength spatial resolution 3D imaging at ultra-fast speed. The subject matter described herein may thus be used in a variety of nanoscale interactions and real-time dynamics of, for example, living cells, neuron networks, etc., that are difficult (if not impossible) to conduct by presently available instrumentations.

Other Implementations

Although a few variations have been described in detail above, other modifications or additions are possible. In particular, further features and/or variations may be provided in addition to those set forth herein. For example, the implementations described above may be directed to various combinations and sub-combinations of the disclosed features and/or combinations and sub-combinations of several further features disclosed above. In addition, the logic flow depicted in the accompanying figures and/or described herein does not require the particular order shown, or sequential order, to achieve desirable results. Other embodiments may be within the scope of the following claims.

What is claimed is:

1. A method comprising:
   generating two or more sequential surface plasmon interference patterns, at least one of the two or more sequential surface plasmon interference patterns being different from another of the two or more sequential surface plasmon interference patterns;
   applying optical radiation at a medium at two or more angles corresponding to the two or more surface plasmon interference patterns, at least one of the two or more angles being different from another of the two or more angles, the medium being configured to generate surface plasmons upon application of optical radiation thereon; and capturing respective images of a specimen resulting from each of the two or more surface plasmon interference patterns.

2. The method of claim 1, further comprising:
generating a reconstructed image of the specimen based on the captured respective images of the specimen resulting form the two or more surface plasmon interference patterns.

3. The method of claim 1, wherein applying optical radiation at the medium comprises:
applying optical radiation comprising two or more optical interference patterns, at least one of the two or more optical interference patterns being different from another of the two or more optical interference patterns.

4. The method of claim 1, wherein applying optical radiation at the medium comprises:
directing the optical radiation at the medium using a modulator to modulate optical energy received by the modulator.

5. The method of claim 4, wherein the modulator comprises one or more of: a digital mirror device, an electro-optical modulator, an acoustic-optical modulator, a liquid crystal modulator, and an optomechanical modulator.

6. The method of claim 1, wherein the medium configured to generate surface plasmons upon application of optical radiation thereon comprises a metal/dielectric interface with at least one surface feature defined thereon.

7. The method of claim 6, wherein the at least one surface features comprises one or more of: at least one slit and at least one grating.

8. A system comprising:
an energy source to generate optical energy;
a controller to cause the generated optical energy to be applied at a medium configured to generate surface plasmons so as to generate two or more sequential surface plasmon interference patterns, at least one of the two or more sequential surface plasmon interference patterns being different from another of the two or more sequential surface plasmon interference patterns, the generated optical energy being applied at the medium at two or more angles corresponding to the two or more surface plasmon interference patterns, at least one of the two or more angles being different from another of the two or more angles, the medium being configured to generate surface plasmons upon application of optical energy thereon; and
a capturing device to capture respective images of a specimen resulting from each of the two or more surface plasmon interference patterns.

9. The system of claim 8, wherein the two or more sequential surface plasmon interference patterns comprise at least one of the two or more plasmon interference patterns having a phase different from another phase of another of the two or more surface plasmon interference patterns.

10. The system of claim 8, further comprising:
a processor to generate a reconstructed image of the specimen based on the captured respective images of the specimen resulting from the two or more surface plasmon interference patterns.

11. The system of claim 8, wherein the controller configured to apply optical energy is configured to:
apply two or more optical interference patterns at the medium, at least one of the two or more optical interference patterns having a pattern different than another pattern of another of the two or more optical interference patterns.

12. The system of claim 8, wherein the controller comprises a modulator including one or more of: a digital mirror device, an electro-optical modulator, an acoustic-optical modulator, a liquid crystal modulator, and an optomechanical modulator.

13. The system of claim 8, further comprising:
the medium configured to generate surface plasmons.

14. The system of claim 8, wherein the medium comprises:
a metal/dielectric interface with at least one surface feature defined thereon.

15. The system of claim 14, wherein the at least one surface features comprises one or more of: at least one slit and at least one grating.

16. An integrated device comprising:
a light source; and
a medium configured to generate surface plasmon interference patterns;
wherein light from the light source is directed at the medium to cause two or more sequential surface plasmon interference patterns to be generated, at least one of the two or more sequential surface interference patterns being different from another of the two or more surface plasmon interference patterns, the generated light being applied at the medium at two or more angles corresponding to the two or more surface plasmon interference patterns, at least one of the two or more angles being different from another of the two or more angles, the medium being configured to generate surface plasmons upon application of light thereon; and
wherein the generated two or more sequential surface plasmon interference patterns resulting in a sequence of images of a specimen that are used to reconstruct a high resolution image of the specimen.

17. The device of claim 16, wherein the light source includes a LED device, and wherein the medium includes a metal/dielectric interface with at least one surface feature defined thereon.

18. The device of claim 16, further comprising:
a controller to modulate the light from the light source and to direct the modulated light at the medium to cause the two or more sequential surface plasmon interference patterns.

* * * * *